US010416045B2

(12) United States Patent
Launiere et al.

(10) Patent No.: US 10,416,045 B2
(45) Date of Patent: Sep. 17, 2019

(54) METHOD FOR HIGH-THROUGHPUT MICRO-SAMPLING ANALYSIS OF ELECTROCHEMICAL PROCESS SALTS

(71) Applicants: Cari A. Launiere, Lemont, IL (US); Candido Pereira, Naperville, IL (US); James L. Bailey, Hinsdale, IL (US); Stanley G. Wiedmeyer, Glen Ellyn, IL (US)

(72) Inventors: Cari A. Launiere, Lemont, IL (US); Candido Pereira, Naperville, IL (US); James L. Bailey, Hinsdale, IL (US); Stanley G. Wiedmeyer, Glen Ellyn, IL (US)

(73) Assignee: UCHICAGO ARGONNE, LLC, Chicago, IL (US)

(*) Notice: Subject to any disclaimer, the term of this patent is extended or adjusted under 35 U.S.C. 154(b) by 245 days.

(21) Appl. No.: 15/237,430

(22) Filed: Aug. 15, 2016

(65) Prior Publication Data
US 2017/0045423 A1 Feb. 16, 2017

Related U.S. Application Data

(60) Provisional application No. 62/205,447, filed on Aug. 14, 2015, provisional application No. 62/309,337, filed on Mar. 16, 2016.

(51) Int. Cl.
G01N 1/12 (2006.01)
C25C 3/34 (2006.01)
(Continued)

(52) U.S. Cl.
CPC ............ G01N 1/125 (2013.01); C25C 3/34 (2013.01); C25C 7/06 (2013.01); G01N 21/71 (2013.01); G01N 23/223 (2013.01); G01N 33/20 (2013.01)

(58) Field of Classification Search
CPC ......... G01N 1/1409; G01N 2001/1436; G01N 1/20; G01N 2001/2028; G01N 21/69;
(Continued)

(56) References Cited

U.S. PATENT DOCUMENTS 2,114,209 A * 4/1938 Boynton ................... B22F 9/06
425/7
2,268,888 A * 1/1942 Mericola .................... B01J 2/02
264/13
(Continued)

OTHER PUBLICATIONS

A. Amirzadeh et al., Producing Molten Metal Droplets Smaller Than the Nozzle Diamerter Using a Pneumatic Drop-On-Demand Generator, Experimental Thermal and Fluid Science, Dec. 20, 2012, pp. 26-33, vol. 47.
(Continued)

Primary Examiner — Benjamin R Schmitt
(74) Attorney, Agent, or Firm — Cherskov Flaynik & Gurda, LLC

(57) ABSTRACT

A method and apparatus for analyzing molten salt electrolyte. The method includes extracting a sample of a molten salt electrolyte from an electrorefiner or other process vessel or conduit; generating droplets from the sample, where the droplets are at a first temperature; transporting the droplets to detectors, where during transport, the droplets attain a second temperature that is lower than the first temperature; analyzing the droplets at or below the second temperature; and returning the droplets to the process. The apparatus includes a droplet generator; a sample transport mechanism; and at least one detector positioned above the sample transport mechanism.

20 Claims, 23 Drawing Sheets

(51) Int. Cl.
*C25C 7/06* (2006.01)
*G01N 21/71* (2006.01)
*G01N 23/223* (2006.01)
*G01N 33/20* (2019.01)

(58) Field of Classification Search
CPC ............. G01N 2021/695; G01N 33/20; G01N 33/206; G01N 2291/0252
USPC ........... 73/61.41, 61.43, 61.55, 61.56, 61.59, 73/64.56, DIG. 9
See application file for complete search history.

(56) References Cited

U.S. PATENT DOCUMENTS

| | | | |
|---|---|---|---|
| 4,841,145 A * | 6/1989 | Wada | G01N 21/35 250/304 |
| 5,820,772 A | 10/1998 | Freitag et al. | |
| 6,073,817 A | 6/2000 | Jairazbhoy | |
| 6,224,180 B1 * | 5/2001 | Pham-Van-Diep | B05B 1/02 347/2 |
| 6,446,878 B1 | 9/2002 | Chandra et al. | |
| 8,877,145 B2 | 11/2014 | Metz et al. | |
| 2003/0119193 A1 * | 6/2003 | Hess | B01F 5/0085 436/44 |
| 2005/0281946 A1 * | 12/2005 | Mergen | B05D 3/0245 427/180 |

OTHER PUBLICATIONS

Nils Lass et al., Enhanced Liquid Metal Micro Droplet Generation by Pneumatic Actuation Based on the StarJet Method, Micromachines, Mar. 11, 2013, pp. 49-66, Issue 4.

Stewart Xu Cheng, Producing Molten Metal Droplets with a Pneumatic Droplet-On-Demand Generator, Jounral of Materials Processing Technology, 2005, pp. 295-302, issue 159.

* cited by examiner

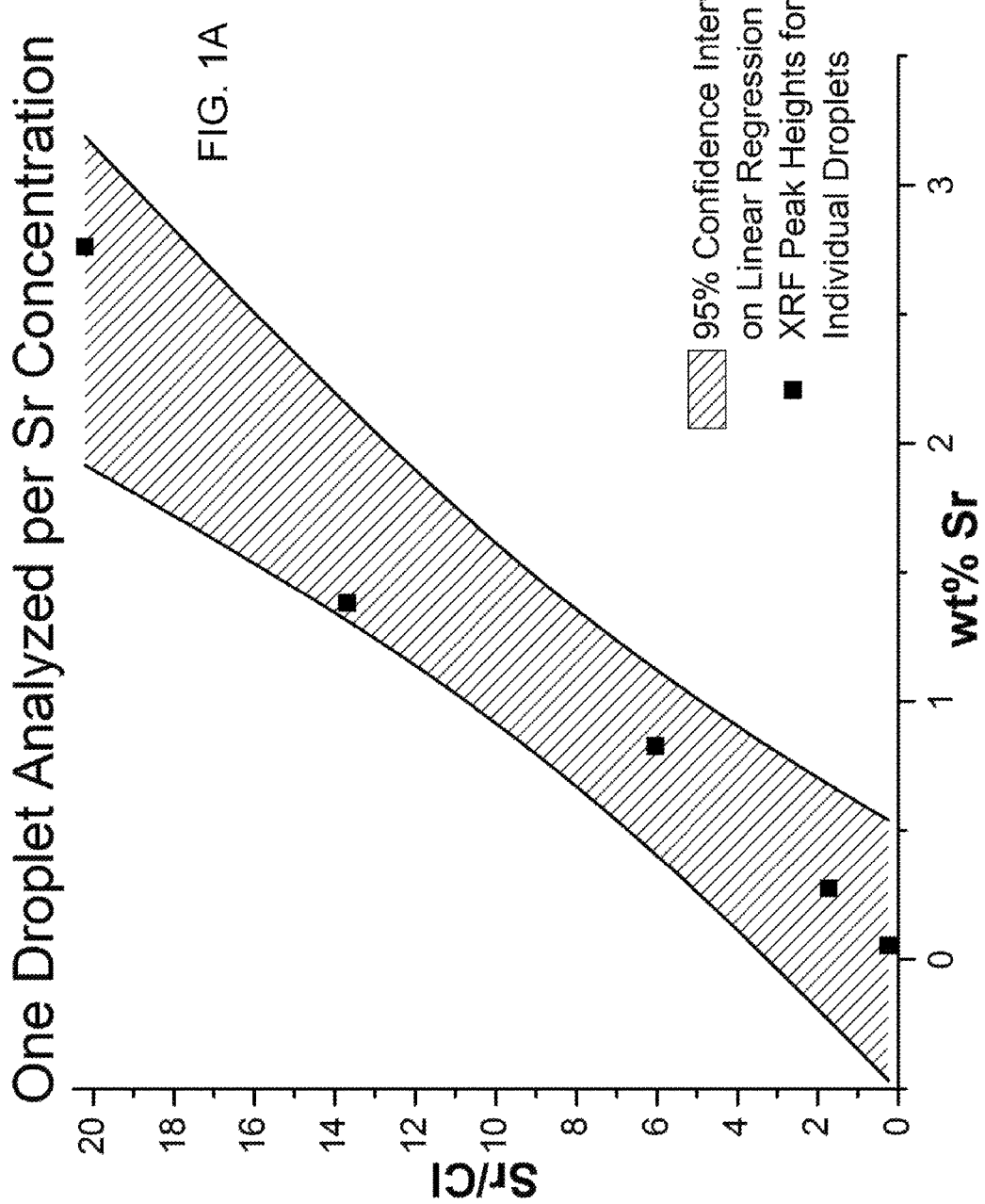

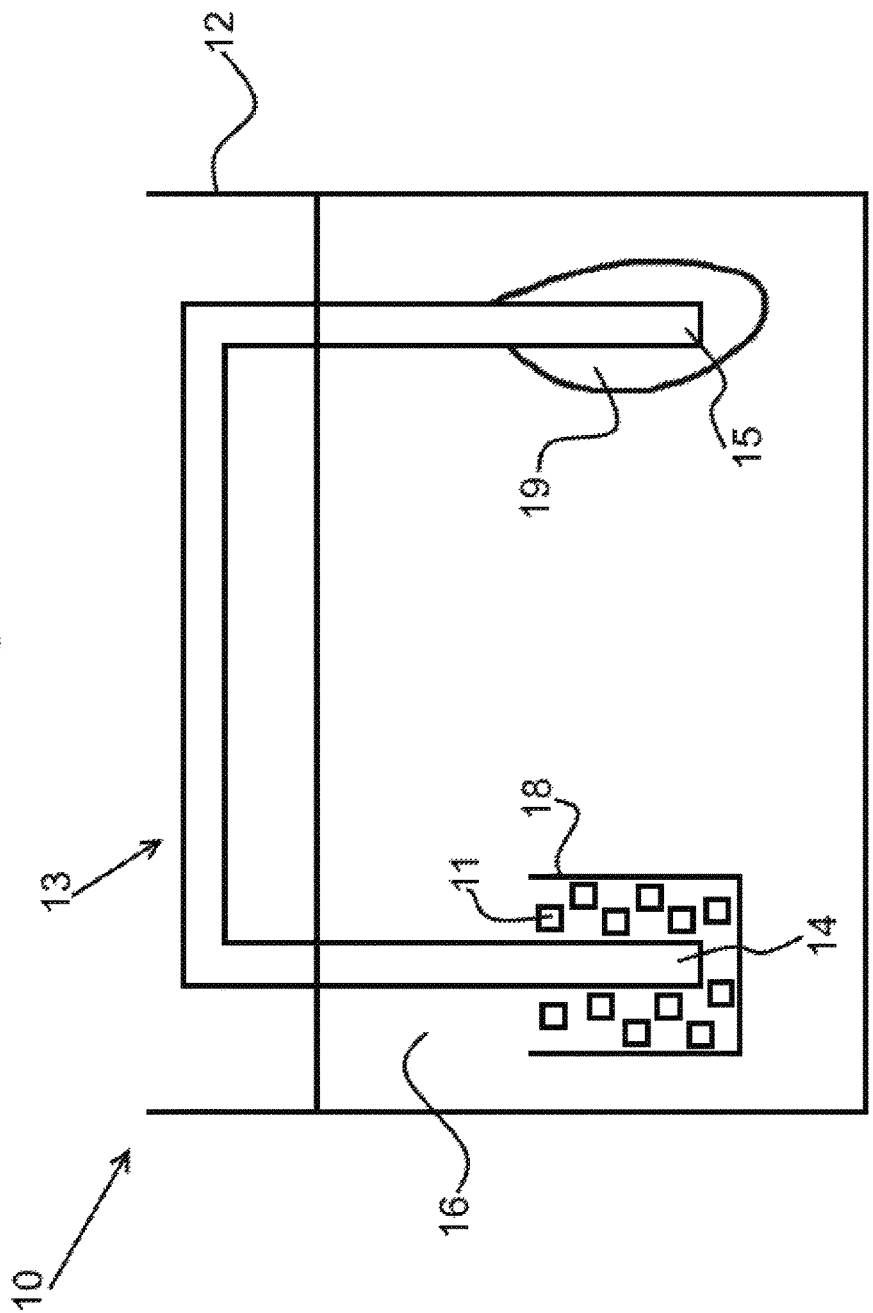

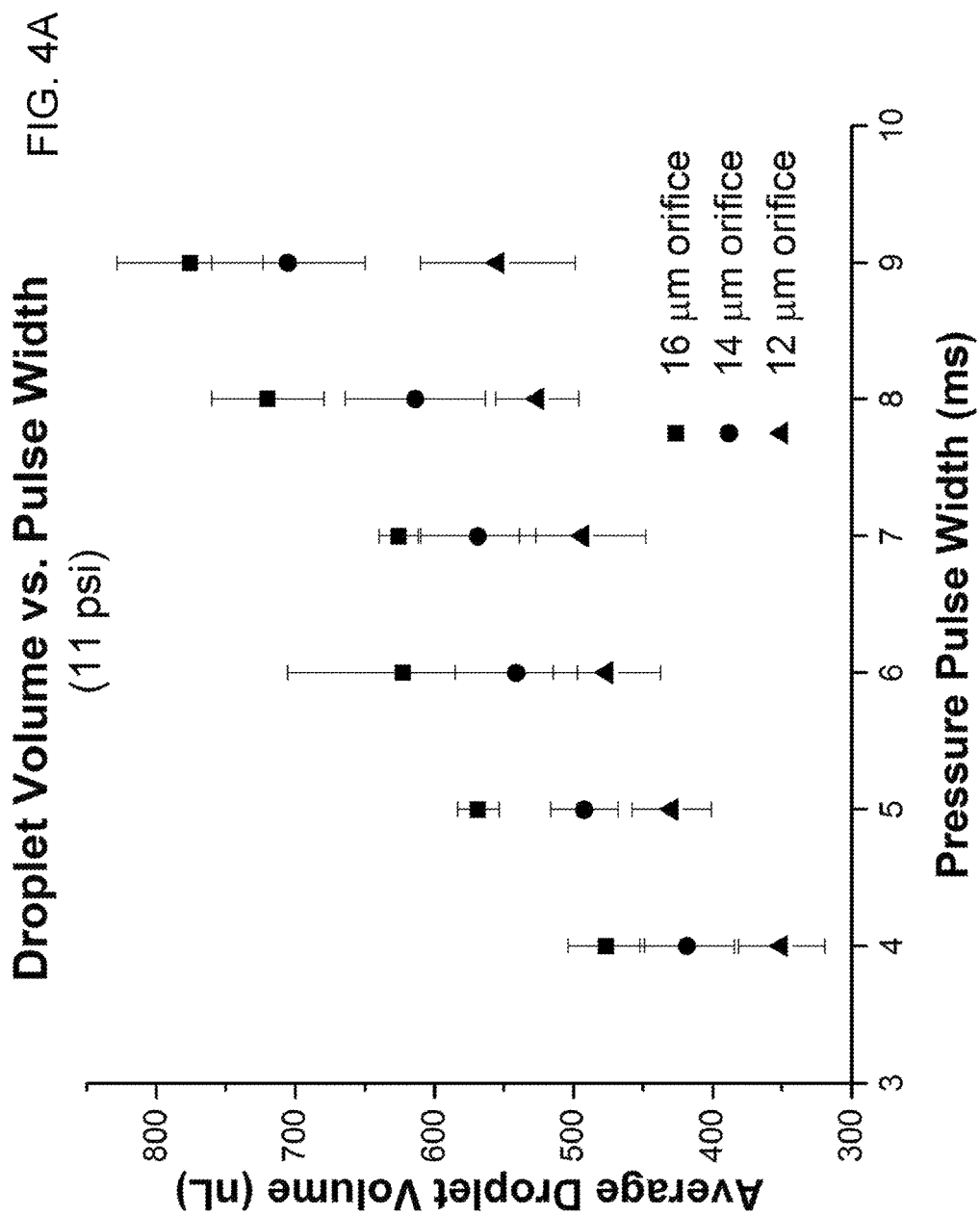

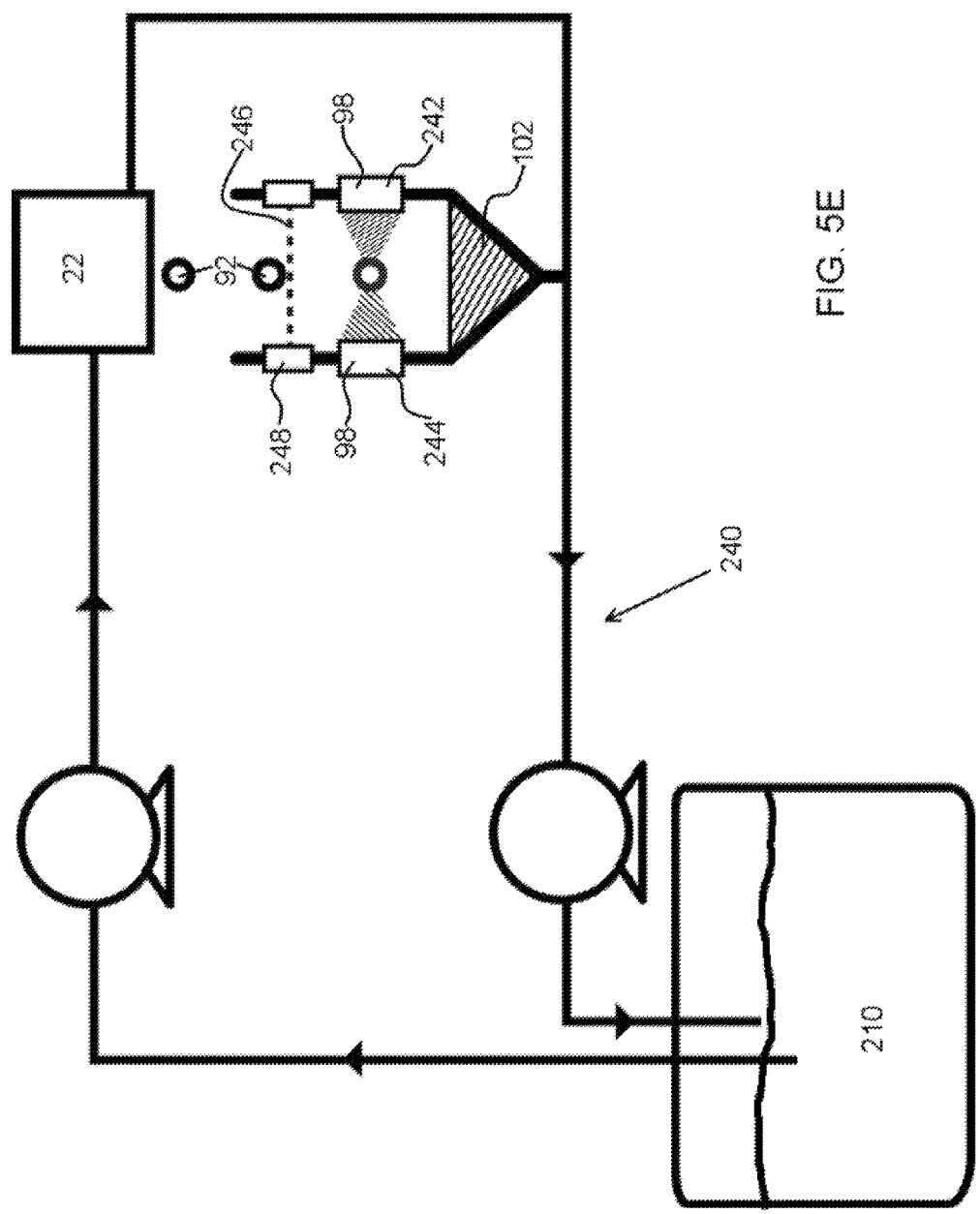

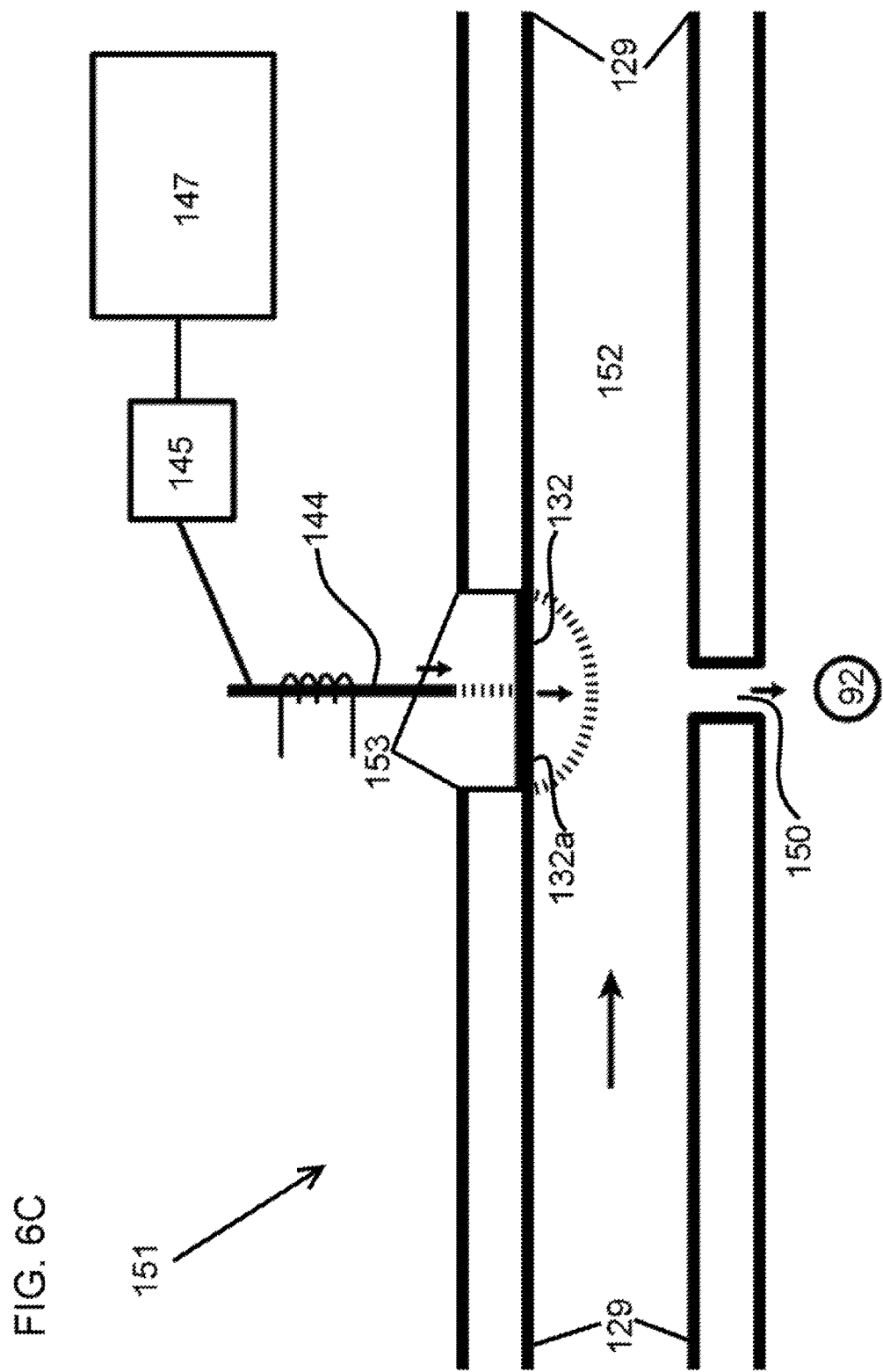

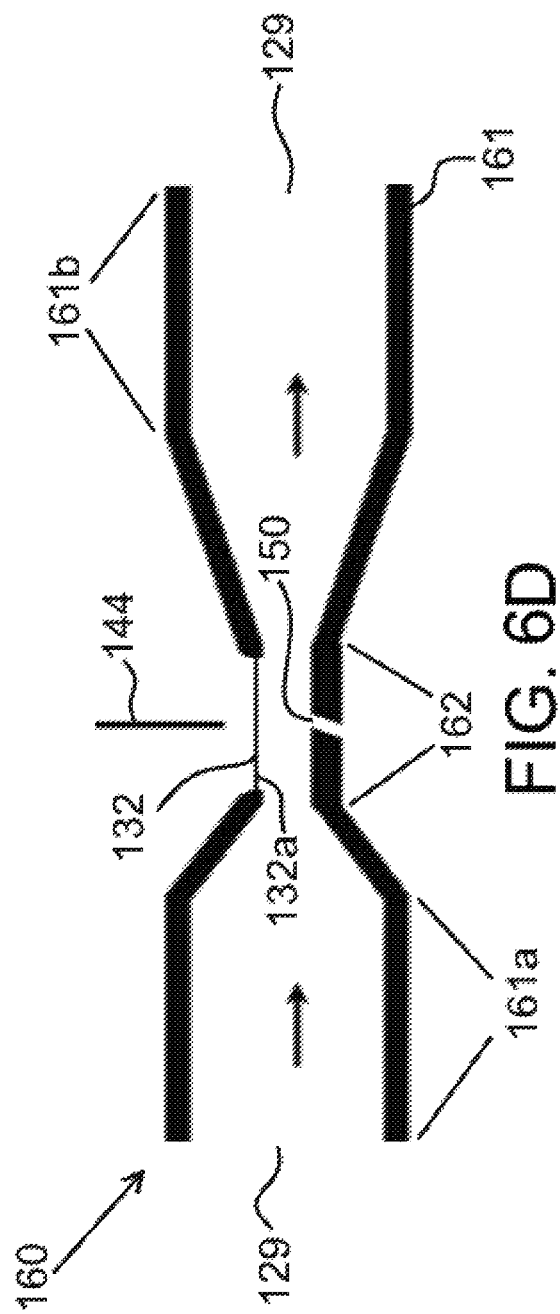

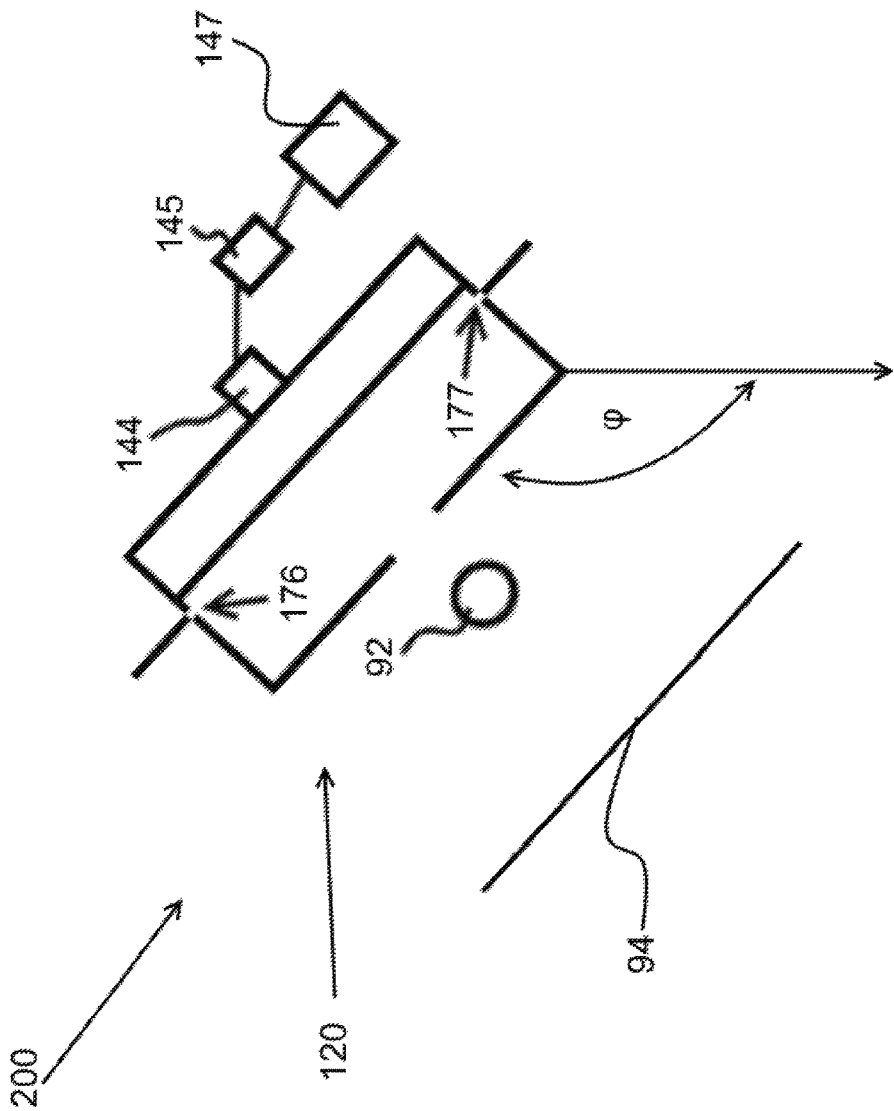

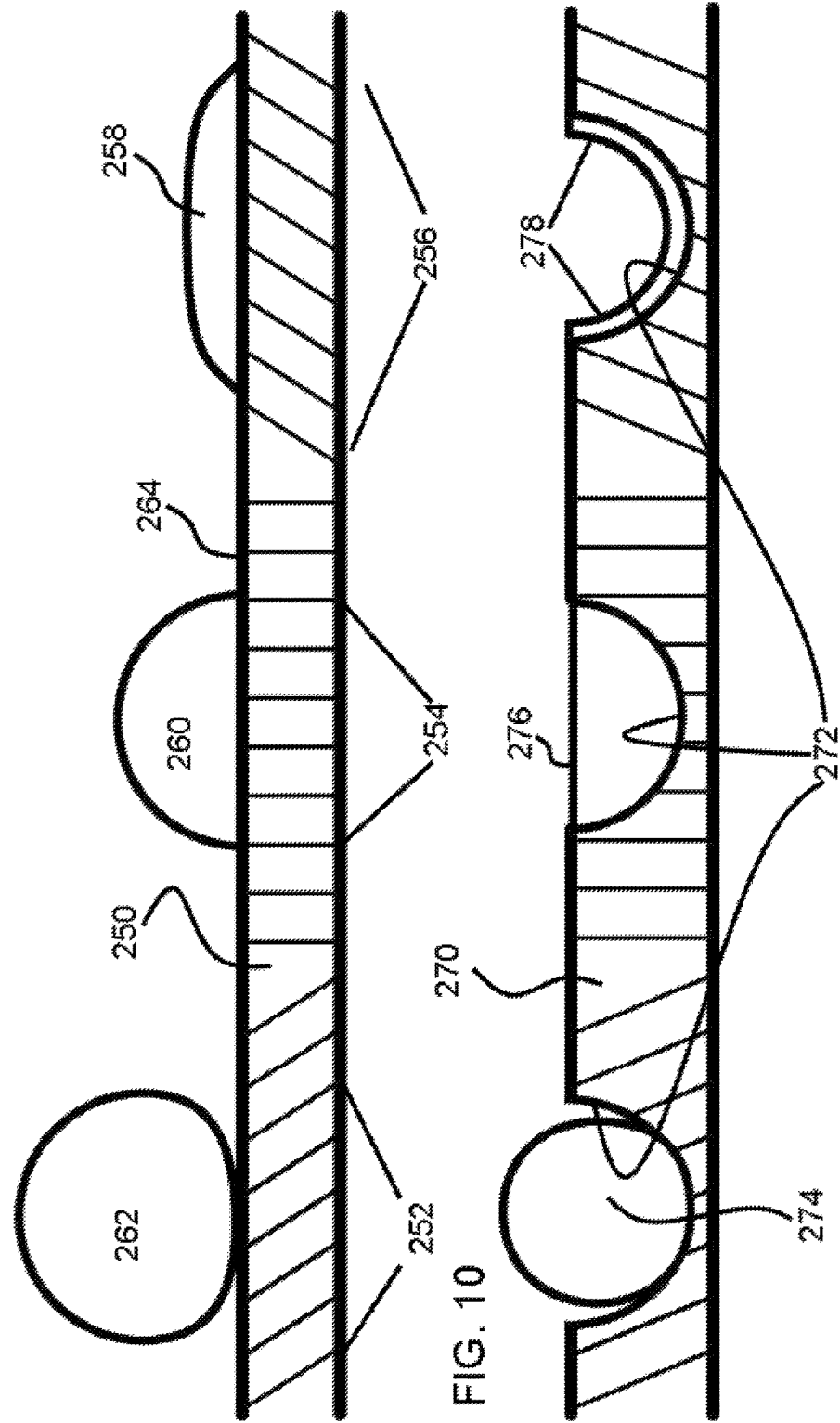

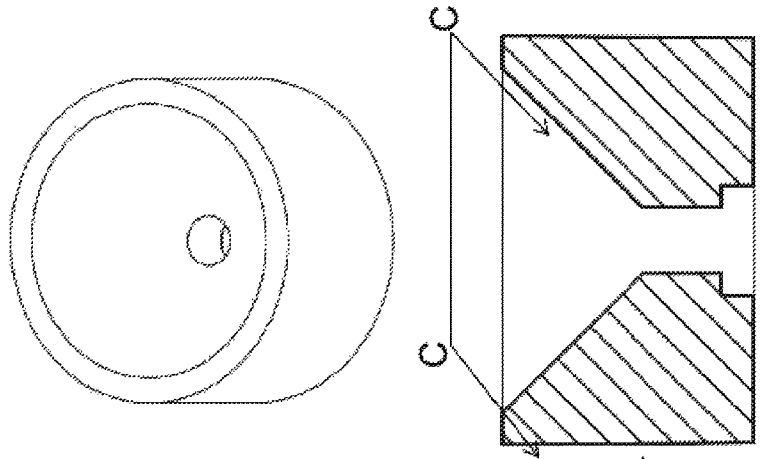
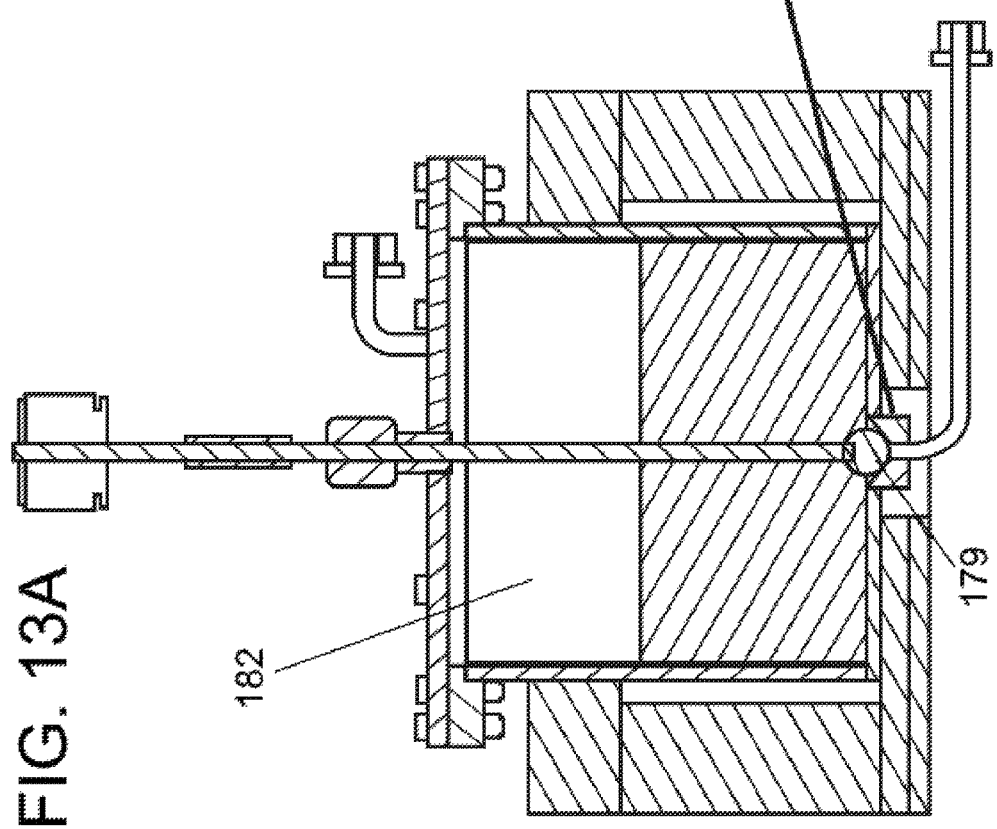

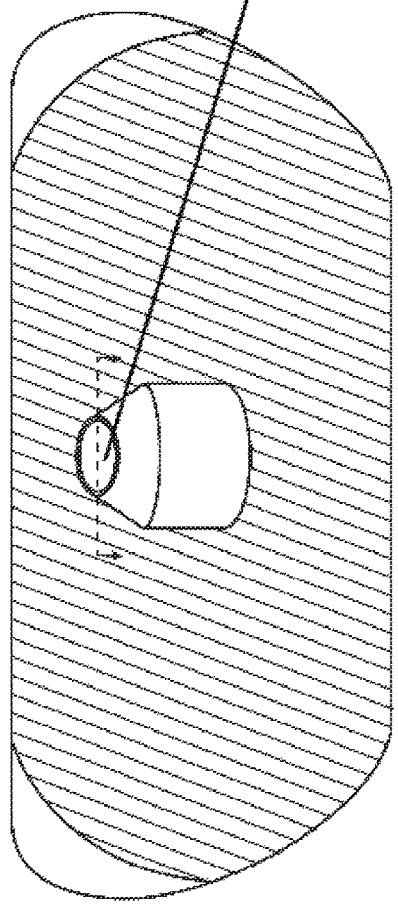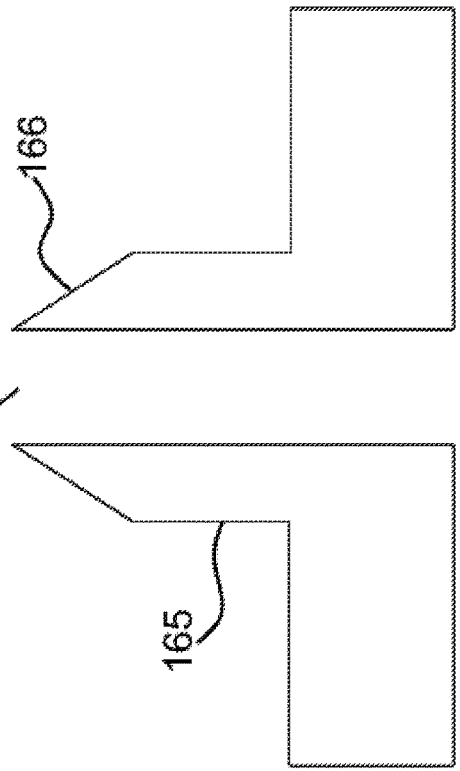

METHOD FOR HIGH-THROUGHPUT MICRO-SAMPLING ANALYSIS OF ELECTROCHEMICAL PROCESS SALTS

PRIORITY

This Utility patent application claims the benefit of U.S. Provisional Patent Application No. 62/205,447 filed on Aug. 14, 2015 and U.S. Provisional Patent Application No. 62/309,337, filed on Mar. 16, 2016, both incorporated in their entirety by reference.

CONTRACTUAL ORIGIN OF THE INVENTION

The U.S. Government has rights in this invention pursuant to Contract No. DE-AC02-06CH11357 between the U.S. Department of Energy and UChicago Argonne, LLC, representing Argonne National Laboratory.

BACKGROUND OF THE INVENTION

1. Field of the Invention

This invention relates to a method for monitoring chemical processes, and more specifically the invention relates to a high-throughput method for micro-sampling and analyzing process fluids.

2. Background of the Invention

Processing used nuclear fuel to separate fission products from valuable fissile and fertile uranium and transuranic elements can be done in a multitude of ways. One way is through electrochemical processing. In electrochemical processing, used uranic nuclear fuel contacts the anode of an electrochemical cell, the electrolyte of which comprises molten salts (often a LiCl—KCl eutectic). When voltage is applied across the anode and cathode, the used nuclear fuel is oxidized at the anode, thereby dissolving into the molten salt electrolyte. At the same time, at the cathode, electrons reduce solvated uranium and plate the uranium onto the cathode. The plated-out uranium can be removed and further purified for use as still-fissile material.

Concurrent with uranium plating onto the cathode, noble metal fission products remain in the anode basket, while most of the other fission products from the used uranic nuclear fuel remain in solution in the electrolyte. These fission products include alkali-, alkaline earth-, rare earth-, and halogen-containing compounds. Used uranic nuclear fuel also contains transuranic elements. All transuranic elements dissolve into the molten salt electrolyte and will co-deposit with uranium on another cathode specifically designed for their recovery. Frequently, after the uranic used nuclear fuel is processed in this way, the electrochemical salts that now contain waste fission products are processed, with the salt being recycled to the process and the waste fission products being incorporated into waste forms for storage in long-term radioactive material repositories.

Available methods for in situ monitoring of electrochemical processing of nuclear materials are limited. High temperatures (500-650° C.) of the molten salt electrolyte solution and radiation emanating from the actinides and fission products present corrosion and radiation barriers to using traditional analytical methods to analyze the bulk electrochemical salt solution in situ. Thus, in situ analysis of the electrochemical salts is generally limited to electroanalytical techniques such as voltammetry. However, molten salt electroanalytical techniques are still under development and so are of limited utility.

As a result of the radiation and high temperatures involved in electroprocessing of used nuclear fuel, elemental and isotopic analysis of electrochemical salts is generally done off-line. Currently, workers, or worker-controlled robots manually take samples of the bulk electrochemical salts from the electrorefiner using fritted tubes. The samples are then removed from the sampling implement, weighed, dissolved in water, and diluted for analysis by techniques such as mass spectrometry.

Manual sampling with off-line analysis has its drawbacks, including the significant time between sampling and analysis, high labor costs, and removing significantly more salt than necessary from an electrorefiner. Additionally, manual sampling of electrochemical salts only allows for a snapshot of the content of the electrochemical salts at the moment a sample is taken. There is also the possibility of a layer of dross on the surface of the electrolyte, which can interfere with the collection of a representative sample by the dip tube method. Taking infrequent manual samples that may not represent the content of the bulk of the electrochemical salts can introduce significant error to the results of monitoring an ongoing electrorefining process. Process monitoring errors can have negative consequences in both process control and in nuclear material accountancy.

A need exists in the art for an on-line, high-throughput method and system of automatically monitoring used nuclear fuel electrorefining processes. The method and system would automatically extract and provide samples of electrochemical process salts in nanoliter (nL, e.g. as little as 10 nL) to several milliliter (mL) volumes (e.g., as much as 10 ml) so as to eliminate exposure of analytical devices and workers to high-temperatures and high radiation levels.

SUMMARY OF INVENTION

An object of the invention is to provide an on-line, high-throughput method for automatically and continuously monitoring used nuclear fuel electrorefining processes that overcomes many of the disadvantages of the prior art.

Another object of the present invention is to provide a method and system for automatic and/or continuous monitoring of molten process solutions, such as those generated in used nuclear fuel electrorefining processes. A feature of the method is the continuous extraction of small volumes of molten material, such as electrochemical process salts from an electrorefiner, that are analyzed at line (for example, where no sample is returned to the feedstream), analyzed on-line (for example, where the analyzed sample is returned to the feed stream) or off-line. An advantage of the method is that numerous samples can be analyzed to accurately monitor an ongoing electrorefining process and reduce statistical error relative to taking a single large sample.

Another object of the present invention is the creation of room-temperature droplets of electrochemical process salts. A feature of the invention is that the droplets can be created in various sizes, for example between about 10 nL and about 10 mL. An advantage of the invention is that these room temperature droplets of electrochemical process salts can be taken off-line for further analysis, for archiving, or for verification analysis by third party regulatory groups.

Yet another object of the invention is to provide an on-line, or an at-line method and system for analyzing an ongoing electrorefining process. A feature of the method is using a droplet generator that delivers samples of electrochemical salts that are between about 10 nL and about 1 mL in scale that rapidly cool to temperatures suitable for analysis. An advantage of the invention is that the aforesaid micro sampling allows for the on-line, or at-line analysis of electrorefining salts using traditional analytical methods without risk of exposing equipment or personnel to high-temperatures and radiation levels.

Still another object of the invention is to provide a semi-continuous, high-throughput method and system for monitoring used nuclear fuel refining processes. A feature of the invention is the use of a droplet generator that can continuously or periodically receive a molten electrochemical process salt stream from a molten salt feedstock, such as an on-line electrorefiner (or other molten salt process vessel, or molten salt transfer line) and continuously or periodically produce small droplets of the process salts to be analyzed. For example, the production of a few hundred samples during a process shift, e.g. 8 hours, is enabled with the invention. An advantage of the invention is that the high throughput nature of sample generation allows for the accurate analysis of an ongoing electrorefining process without the sampling and analysis errors associated with a single large sample. Another advantage of the invention is that the unused volume of the electrochemical process salt stream to the droplet generator returns to the process, avoiding excess sampling waste and the need to replenish electrochemical salts to the electrorefiner. A further advantage of the invention is that it creates droplets of molten salt (initially 450° C.-700° C.) that are small enough in volume to facilitate rapid cool down to temperatures low enough (e.g. suitably at or below about 150° C., preferably below about 80° C., and most preferably below about 30° C., such as at room temperature) to avoid damage to analysis equipment and allow a wide range of on-line, at-line, or off-line analysis techniques to be used. Droplets can cool to ambient temperature between about 3 seconds and about one minute after their formation, depending on their size and the ambient temperature around the droplet generator.

Yet another object of the invention is to provide an automated method and system for anytime monitoring of used nuclear fuel refining processes. A feature of the invention is the creation of room-temperature droplets of electrochemical process salts. An advantage of the invention is that these room temperature droplets of electrochemical process salts can be taken off-line for further analysis when necessary. Analysis can occur at room temperature.

Still another object of the invention is to provide an automatic method for monitoring used nuclear fuel refining processes. A feature of the invention is the use of a system that automatically extracts electrochemical process salt samples from an electrorefiner (or other process vessel or molten salt transfer line), delivers the samples to detectors, and returns the samples to the process. An advantage of the invention is that it reduces the need to transport salt samples off-line for analysis, thereby reducing radiation and thermal risks to workers and reducing the time needed for sample analysis.

Briefly, the invention provides a method for analyzing molten salt electrolyte, the method comprising the automated steps of extracting molten salt electrolyte from a molten salt process solution; generating droplets of the sample of molten salt electrolyte, wherein the droplets are less than about 10 mL in volume; and analyzing each of the droplets of salt. In an embodiment of the method, all of the droplets are about the same volume.

Also provided is a method for analyzing molten salt electrolyte, said method comprising the steps of extracting a sample of a molten salt electrolyte from an electrorefiner (or other molten salt process vessel, or molten salt transfer line); generating droplets from the sample, wherein the droplets are at a first temperature; transporting the droplets to detectors, wherein during transport, the droplets attain a second temperature that is lower than the first temperature; analyzing the droplets at or below the second temperature; and returning the droplets to the process.

The invention also provides a system for analyzing molten salt electrolyte comprising a droplet generator defining a longitudinal axis, and also defining a depending end forming an aperture; a transport belt comprising a substrate having a first surface wherein the first surface opposes the aperture surface, a second surface, and a longitudinal axis extending in a direction substantially perpendicular to the longitudinal axis of the droplet generator; a plurality of rollers adapted to rotate around their longitudinal axes, wherein the second surface of the substrate is in frictional contact with said rollers, and wherein at least one of said rollers is motorized to cause movement of the substrate in a direction perpendicular to the longitudinal axis of the droplet generator; and at least one detector having a longitudinal axis positioned above the first surface of the substrate such that the longitudinal axis of the at least one detector is substantially parallel to the longitudinal axis of the droplet generator.

BRIEF DESCRIPTION OF DRAWING

The invention together with the above and other objects and advantages will be best understood from the following detailed description of the preferred embodiment of the invention shown in the accompanying drawings, wherein:

FIG. 1A is a calibration plot showing the wide confidence interval associated with analyzing one sample per analyte concentration;

FIG. 2 depicts an elevated view of an electrorefiner for used nuclear fuel of the type that can be used in conjunction with the present invention;

FIG. 4A is a graph showing salt drop volume as a function of time that a drop generator egress valve remains activated, in accordance with features of the invention;

FIG. 4B is a graph showing salt drop volume as a function of supply pressure, in accordance with features of the present invention;

FIG. 5E is a schematic view of an on-line system for monitoring an ongoing electro refining process by analyzing droplets immediately after generation, in accordance with features of the invention;

FIG. 6C is a detail view of an alternative embodiment of the flow cell of FIG. 6B, in accordance with features of the invention;

FIG. 6D is a detail view of an alternative embodiment of the flow cell of FIG. 6C, in accordance with features of the invention;

FIG. 8 is a detail view of a continuous, low-flow embodiment of the system shown in FIG. 6, in accordance with features of the invention;

FIG. 9 is a side view of a customizable conveyor substrate, in accordance with features of the invention;

FIG. 10 is a side view of a 3-dimensional customizable conveyor substrate, in accordance with the features of the invention;

FIG. 13A is a cross sectional view of a salt reservoir, in accordance with features of the present invention;

FIG. 13B is a cross sectional view of a drain assembly of the salt reservoir depicted in FIG. 13A, in accordance with features of the present invention FIG. 13C is a view of FIG. 13B along line C-C;

FIG. 15A is a picture of an orifice utilized in conjunction with the alternative droplet generated, in accordance with features of the present invention; and FIG. 15B is a view of FIG. 15A taken along line B-B.

DETAILED DESCRIPTION OF THE INVENTION

Figure 1B:
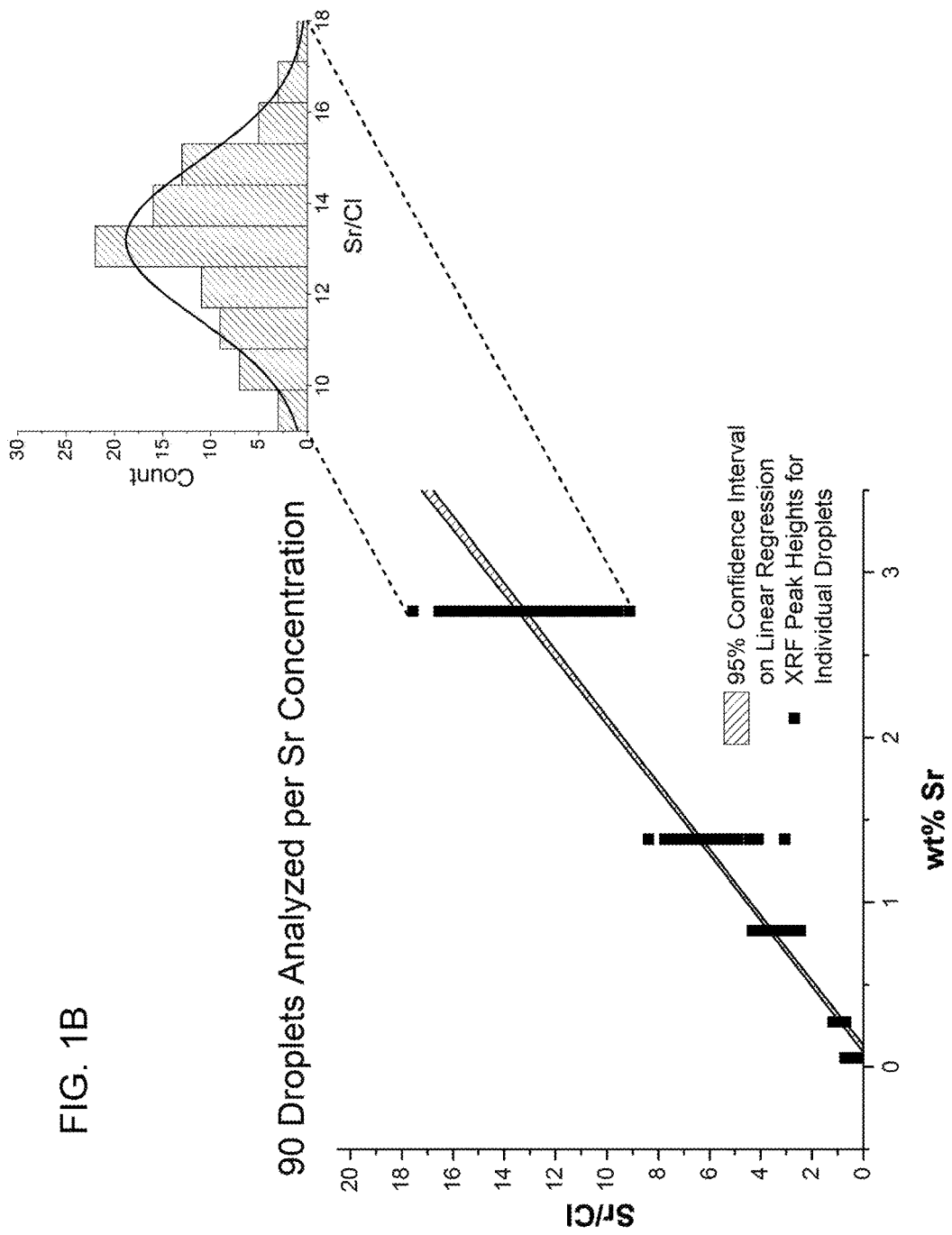
FIG. 1B is a calibration plot showing the narrow confidence interval associated with analyzing 90 samples per analyte concentration, in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides on-line monitoring of electrorefining of used nuclear fuel. Particularly, the invention provides monitoring of electrorefining salt utilized during processing of used enriched uranium fuel. The invention generates single uniform droplets on demand. The invention can generate different size (e.g. non-uniform) droplets or multiple droplets at the same time.

An embodiment of the invention utilizes a pneumatic droplet generator, which balances an applied pressure with surface tension at a sample egress point or orifice to control droplet generation and regulate sample size. Droplet sizes ranged from about 10 nL to about 10 mL. This large sample size range of the pneumatic droplet generator embodiment makes it ideal for generating samples for off-line analysis and processing, as a variety of sample sizes will be required to accommodate the different specific analysis techniques.

Another embodiment of the invention generates droplet samples through an orifice in a sampling loop by manipulating fluid pressure at the sample egress port or orifice according to fluid dynamics principles. This embodiment relies on the Venturi effect to maintain an orifice region that is at atmospheric pressure or at a slight vacuum relative to atmospheric pressure to prevent fluid from leaking out the orifice in-between droplet actuation events. In one embodiment of the fluid pressure droplet generator, droplet generation is actuated by increasing fluid pressure at the orifice by deflecting a diaphragm inwards. In another embodiment of the fluid pressure droplet generator, droplet generation is actuated by increasing the fluid pressure at the orifice by increasing back pressure by reducing the cross sectional area downstream of the orifice.

The fluid pressure droplet generator embodiment of the invention is leak proof as there is no pressure driving force at the orifice in-between droplet generation events (as opposed to the pneumatic droplet generator embodiment where a pressure driving force, due to gravity and hydraulic head, is balanced by surface tension to prevent leaking). However, the fluid pressure droplet generator embodiment has a smaller range of possible sample sizes (approximately 10 nL to 500 µL). Therefore, the fluid pressure embodiment is better suited to continuous operating conditions of on-line or at-line monitoring as leak resistance is very important for this type of operation.

The fluid pressure embodiment utilizes stainless steel orifices, which can be easily re-bored to remove deposits. Also, the fluid pressure system is less dependent on surface tension (and therefore sample composition), compared to the pneumatic embodiment of the invented system.

The systems will operate at a variety of pressure ranges depending on the parameters required for any given application. The pneumatic system would generally operate between a slight vacuum (e.g., greater than 10 mtorr) in the chamber during the pressure oscillations that occur during droplet generation and 200 psi, but preferably up to about 30 psi. The fluid pressure system would generally operate between 0.1 mtorr (for the vacuum filled embodiment) or a slight vacuum (e.g., greater than 10 mtorr) at the orifice region for all fluid pressure embodiments and 100 psi, but preferably up to about 20 psi.

There are two categories of species in the electrochemical process salt: major constituents (LiCl or LiCl—KCl eutectic, by definition 56% KCl by weight) and fuel derived elements (U, Pu, Cs, Sr, La, Ce, etc.). The above-stated salts are provided not to be limiting but to give examples of salts and elements that are suitable for use in conjunction with the instant invention.

In addition, the invention is suitable for on-line composition monitoring of processes using molten materials as fuels. For example, the invention is suitable for use in monitoring the composition of molten thorium-uranium fluoride salts used in molten salt reactors.

The invention is also suitable for use in monitoring of other processes using molten materials. For example, the invention provides a method for analysis of liquid sodium in nuclear reactors using liquid sodium coolant. The invention is also suitable for use in monitoring electrorefining of non-nuclear materials such as aluminum, copper and other metals.

The invention is also suitable for use in monitoring other processes where the liquids are not at elevated temperatures. Generally, a suitable temperature range is from the melting point of the sample material to the vapor point of the sample material. With typical hardware, temperatures up to approximately 800° C. are suitable, but judicious choices of hardware constituents can increase that ceiling.

A salient feature of the present invention is its high-throughput capacity. Each sample droplet produced using the instant invention has a volume of approximately 1 μL. With small sample volumes, large numbers of molten salt electrolyte samples may be drawn indefinitely at regular or irregular intervals from an active electrorefiner or other molten salt feed stream without having a noticeable impact on the process. Further, using the instant invention, many samples of molten salt electrolyte can be analyzed continuously and on-line such that an active electrorefiner can be continuously monitored by analyzing each sample before returning it to the electrorefiner.

In an alternative embodiment, sampling is done semi-continuously such that as few or as many samples may be extracted as desired over any length of time during which the salt is in fluid state. For example, several samples, or several hundred samples may be generated within a specific time frame.

With high-throughput monitoring of an ongoing used nuclear fuel refining process, the instant invention reduces statistical error that is inherent with traditional monitoring methods.

In state of the art sampling methods, workers manually retrieve discrete samples of molten salt electrolyte. Inasmuch as this manual harvesting is somewhat intensive, and dangerous, samples are drawn infrequently, and certainly not semi-continuously or automatically. These discrete samples introduce error into the monitoring of an ongoing used nuclear fuel monitoring process because of the significant time between sampling and analysis, and between measurements. In addition, the random variability associated with a set of measurements is related by the following equation:

$$CI = x + t^* \frac{s}{\sqrt{n}}$$

where CI represents the confidence interval for the set of measurements, X is the mean value of the samples measured, $t^*$ is the distribution representing the sample population, s is the standard deviation of the measured values, and n is the number of samples.

The invention narrows the confidence interval for the composition measurements of electrochemical salts when compared to analyzing small numbers of samples. The confidence interval narrows as the number of random samples analyzed from a population increases. The "true" value lies within an interval about the mean value of the samples measured with some degree of confidence, typically 95 percent, defined by the statistical distribution. Since the present invention enables generation of a large number of microliter or smaller droplets, one can generate a thousand microliter samples rather than a single milliliter sample. Analyzing salt composition for a thousand microliter samples will narrow the confidence interval by a factor of 31 compared to analyzing a single sample because random measurement and sampling errors are averaged out.

FIGS. 1A and 1B demonstrate the effect of the invention's high-throughput sampling and analysis capabilities on measurement confidence intervals. These calibration curve plots show data for X-ray fluorescence analysis of salt droplets generated with the pneumatic droplet generator embodiment of the invention. LiCl—KCl eutectic salts were doped with different concentrations of $SrCl_2$, then the invention was used to generate and analyze micro-samples of the salts. The Sr peak height measurements (normalized to Cl peak height measurements) are plotted against known Sr weight fractions in FIGS. 1A and 1B. When a single droplet is analyzed per Sr concentration or harvesting event (analogous to traditional sampling where often only a single sample is taken), there is a large amount of measurement uncertainty, as seen in FIG. 1A. When 90 droplets are analyzed per Sr. concentration (FIG. 1B), the measurements have a wide distribution, however, that distribution is centered on a mean that converges neatly into a linear calibration curve with a tight confidence interval.

Another salient feature of the invention is the automation of monitoring an ongoing used nuclear fuel electrorefining process. In an embodiment, a single controller controls the sampling and analyzing process without the need for human intervention. This reduces the complexity of a system to monitor an ongoing electrorefining process and limits the number of elements of the system that can breakdown or malfunction.

An embodiment of the invention analyzes molten salt and salt mixtures. "Molten" means that the subject salt or salt mixture is substantially liquid and at a temperature at or greater than the melting point of the salt mixture. Other embodiments of the invention facilitate analysis of a molten salt or salt mixture where substantially all (e.g., approximately 95 percent) of the salt is in liquid phase when the molten salt is initially deposited onto a transom for subsequent nondestructive and/or destructive testing. "Molten" includes compositions that are primarily liquid but contain some amount of entrained solid particles. As long as the egress orifice of the droplet generator utilized in the instant method is not substantially blocked, the presence of such solids is not problematic. An embodiment of the invention includes filtering means to prevent larger entrained solids (those that are large enough to clog the orifice) from entering the droplet generator system. For example, placing a filter in the molten supply feed pipe will prevent such solids from blocking the orifice.

Specifically, the inventors have discovered that using a droplet generator to create droplets having micro- or nano-liter volumes (e.g., between approximately 10 nL and approximately 10 mL) of electrochemical process salts used in the electrorefining of used nuclear fuel allows for rapid cooling of the salts. This rapid cooling of the salts allows for an on-line analysis of an ongoing used nuclear fuel electrorefining process.

In an embodiment of the invention, a droplet generator uses molten salt extracted from an electrorefiner to make small droplets that cool rapidly (e.g., to ambient temperature within approximately 30 seconds) which are then analyzed using various analytical devices.

FIG. 2 is an elevated view of an electrorefiner, designated as numeral 10, for refining used nuclear fuel 11. Generally, the electrorefiner 10 comprises a container 12 for housing, enclosing or otherwise containing the constituents of an electrochemical cell 13. The cell 13 comprises an anode 14 and cathode 15, both submerged in electrolyte solution 16. In an electrorefiner 10 of the type used to refine used nuclear fuel 11, an anode basket 18 is loaded with used nuclear fuel 11 and is positioned within the container 12 such that the used nuclear fuel 11 is in electrical contact with the anode, and in fluid communication with the electrolyte solution 16. Used nuclear fuel 11 is inserted in the basket 18 in small pieces to expose maximum surface area of the used fuel 11.

The used nuclear fuel 11 comprises fissile and non-fissile uranium, transuranic elements, and fission products such as alkali, alkali earth, rare earth, and halogen elements. The electrolyte solution 16 comprises molten salt or a combination of molten salts and a dissolved actinide chloride or combination of actinide chlorides such as $UCl_3$. When a voltage is applied between the anode 14 and cathode 15, uranium contained in the used nuclear fuel 11 is oxidized, dissolving the fuel 11 into the electrolyte solution 16. The uranium that dissolves into the electrolyte solution 16 with the application of voltage is reduced at the cathode 15 and thus plates onto the cathode 15 along with some amount of transuranic elements (plated elements shown as element number 19 in FIG. 2). The uranium and transuranic elements once contained in the used nuclear fuel plates onto the cathode 15, and much of the other elements that comprised the used nuclear fuel remain in the electrolyte 16.

Pneumatic Droplet Generator Detail

To monitor the electrorefining of used nuclear fuel using the type of electrorefiner shown in FIG. 2, samples of electrolyte solution 16 are analyzed for elemental and isotopic composition.

Figure 3A:
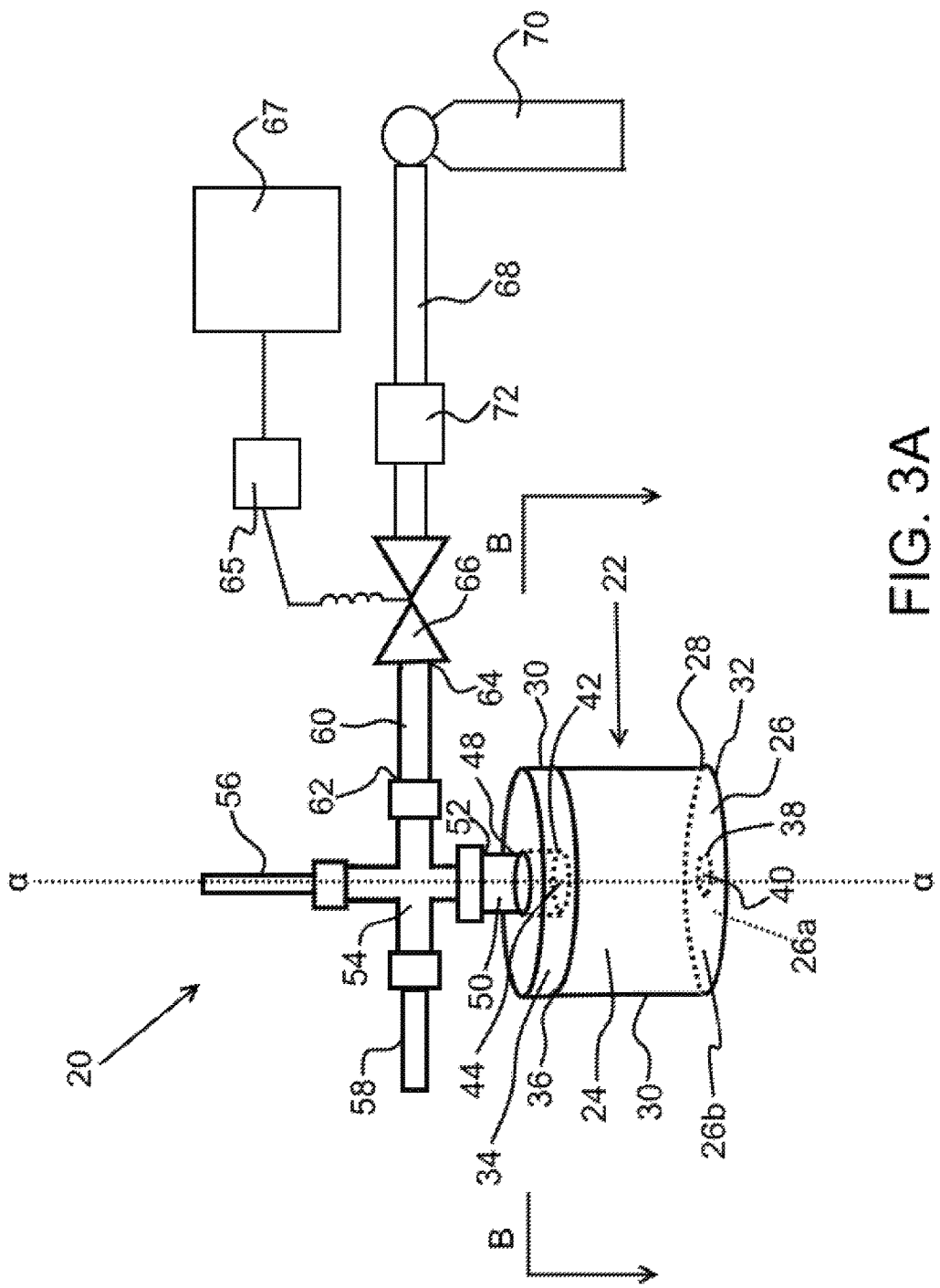
FIG. 3A is a schematic of a system for producing droplets of electrochemical salts, in accordance with the features of the present invention.

FIG. 3A depicts a schematic of a system, designated as numeral 20, for generating droplets of electrochemical salts used in electrorefining used nuclear fuel. The system 20 comprises a droplet generator 22 comprising a reservoir 24 adapted to receive molten salt. The reservoir 24 is defined by a bottom substrate or floor 26 and walls 30.

The reservoir is depicted as cylindrical for illustrative purposes only, inasmuch as any container or conduit adapted to receive molten material is suitable. The floor 26 (in this instance circular in shape) defines a first downwardly facing surface 26a and second upwardly facing surface 26b. A first end 28 of a cylindrical wall 30 having an interior and exterior surface is integrally molded to the outer edge 32 of the second surface 26b of the floor 26. A circular lid 34 is removably attached to the second end 36 of the cylindrical wall 30 such that a cylindrical void is created between the floor 26, the interior surface of the cylindrical wall 30, and the medially-facing surface of the circular lid 34. The volume of the molten salt reservoir is from about 0.1 mL to about 1000 mL, preferably from about 1 mL to about 50 mL, and most preferably from about 2 mL to about 10 mL.

In an embodiment, the circular bottom 26 and cylindrical wall 30 of the droplet generator 22 can be molded as a single piece. The droplet generator 22 can be made from materials that will not degrade, deform, or melt when subjected to temperatures up to 400-700° C. Suitable materials include stainless steel, low carbon steel, glassy carbon, tantalum, niobium, yttria, zirconia, alumina, silicon nitride, silicon carbide, hafnium nitride, hafnium oxide, strontium ruthenate, lithium ruthenate and combinations thereof.

A salient feature of the invention is its suitability for use with many types of molten materials. In an embodiment, the interior of the droplet generator 22 is coated with an inert material to prevent corrosion associated with a particular molten moiety. Suitable coating materials include carbon, boron doped diamond, hafnium nitride, hafnium oxide, zirconium oxide, and combinations thereof.

The circular bottom 26 of the droplet generator 22 further comprises a first aperture 38 that transverses the thickness of the floor 26 so as to confer fluid communication between the interior and exterior of the container 22. In an embodiment of the invention, the aperture 38 is concentric with the longitudinal (e.g. vertically disposed) axis α of the generator and/or with a circular floor. In an embodiment of the invention the aperture 38 is composed of an orifice that is a different material than the droplet generator chamber material.

The orifice may be held in the aperture by means of a friction fit, by a threaded fitting, by fastener or by any combination of these. Suitable orifice materials include sapphire, alumina, cubic zirconia, glassy carbon, yttria, yttria stabilized zirconia, yttrium aluminum garnet and combinations thereof.

The aperture or orifice may be coated with a material to achieve chemical compatibility/corrosion resistance and desired wettability of the aperture or orifice by molten salt. Specifically, suitable orifice or orifice coating materials are not wetted strongly by the fluid being sampled. If the orifice material is wetted too strongly, fluid surface tension will not be sufficient to prevent salt from flowing through the orifice in between droplet generation actuation events. Suitable coating materials include, but are not limited to, boron doped diamond, hafnium nitride, hafnium oxide, zirconium oxide, cubic zirconia, and combinations thereof.

Similarly, the circular lid 34 of the droplet generator 22 further comprises a second aperture 42 extending through the thickness of the lid 34 at the center 44 of the lid 34 such that the aperture is concentric with the lid 34. A band heater 46 (shown in FIG. 3B) overlays exterior surfaces of the droplet generator 22 as to maintain molten salt contained thereby in a molten state. In an embodiment of the invention, the first and second apertures are coaxially aligned with the vertically disposed axis of the generator.

A first end 48 of a conduit 50 is reversibly coupled to the circular aperture 42 in the lid 34 of the droplet generator 22 so as to be in fluid communication therewith. The second end 52 of the conduit 50 is removably coupled to a four-way cross-junction 54 such that the interior of the droplet generator 22 is in fluid communication with the cross junction 54. A suitable means for such reverse coupling includes a male-female threaded configuration, a snap fit configuration, quickly-connect configurations and combinations thereof.)

The port of the cross-junction 54 opposing the port coupled to the conduit 50 is reversibly coupled to a gas vent with an adjustable flow valve 56. One port of the cross-junction 54 at a right angle to the port coupled to the droplet generator 22 is coupled to a pressure transducer 58 to monitor the pressure within the droplet generator 22. The final port of the cross-junction 54 is coupled to a conduit 60 having a proximal end 62 and distal end 64. At the distal end 64 of the conduit 60, the conduit 60 is coupled to a normally closed solenoid valve 66 in electronic communication with a power source 65 controlled by a controller 67. Upstream from the normally closed solenoid valve 66, a second conduit 68 couples the solenoid valve 66 with an inert gas source 70. A manometer 72 is coupled to the conduit 68 intermediate the solenoid valve 66 and the inert gas source 70 to monitor the pressure in the conduit 68. In an embodiment, a line regulator is coupled between the inert gas source 70 and the manometer 72 to regulate the pressure in the second conduit 68 to a pressure lower than the pressure generated by the inert gas source 70 without regulation. For example, an inert gas source can be set to output gas at a pressure of 10-50 psi. A line regulator can be used to drop this pressure to pressures in the range of about 0.5 to about 20 psi.

Figure 3B:
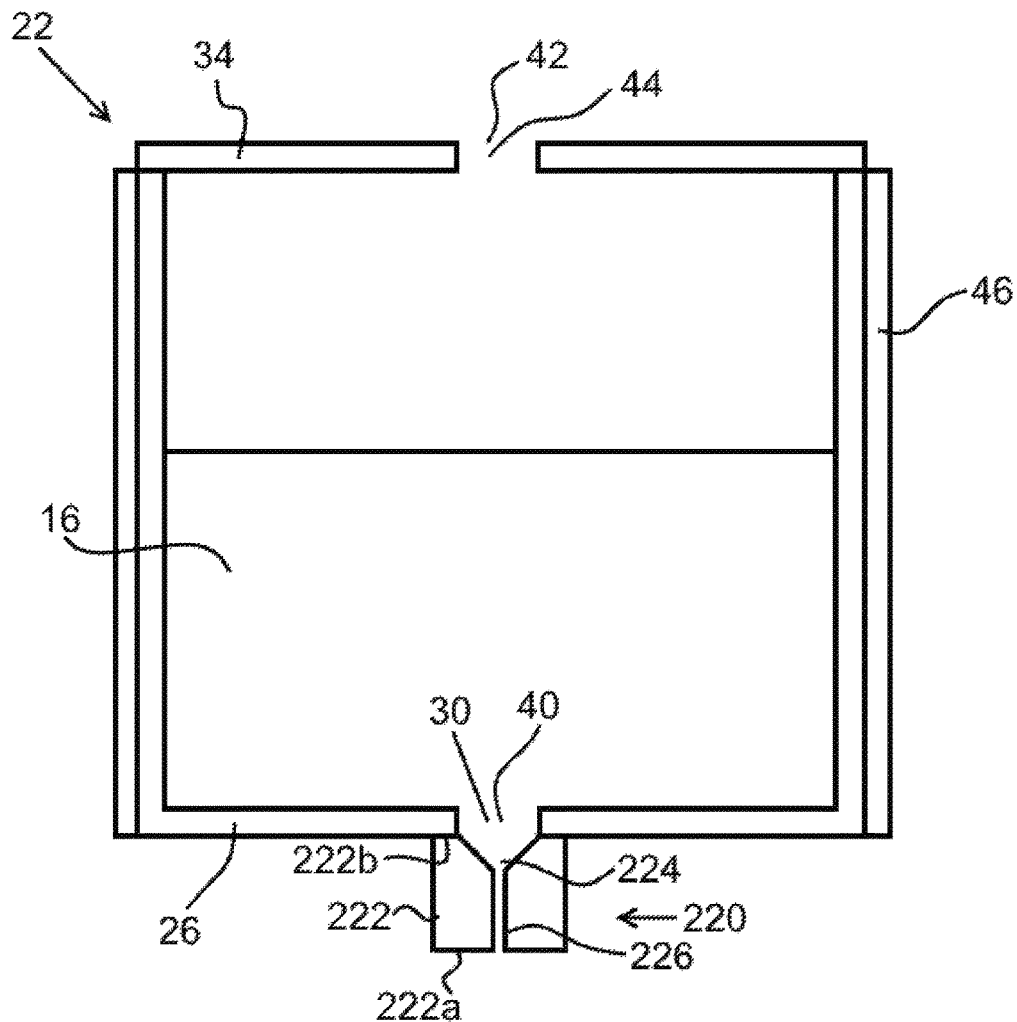
FIG. 3B is a view of FIG. 2A taken along line B-B, in accordance with the features of the present invention.

FIG. 3B is a detail view of the droplet generator 22 of FIG. 3A. In operation, the droplet generator 22 is loaded with molten salt electrolyte solution 16 (so depicted in FIG. 2.) The droplet generator 22 is heated to maintain the molten state of molten salt electrolyte solution 16 residing within the generator. Any heating means suitable to maintain the salt above its melting point is suitable. Suitable heating means include those residing in the interior of the generator so as to heat the salt via direct contact, or those which reside outside of the generator, so as to heat the salt via thermal conductance through the walls of the generator. Suitable heating means include, but are not limited to electrical resistance heaters and combustion heaters to impart heating from the exterior of the generator through thermal conductance, induction heaters which reside within the generator and directly contact the salt, and combinations thereof.

In one embodiment, a band heater 46 is positioned outside the generator 22 so as to be in thermal communication with it. The band heater may be in physical contact with an outside surface of the generator 22 so as to heat the electrolyte solution 16 via thermal conductance through the walls of the generator. In an embodiment, an insulating material such as a ceramic fiber is positioned in thermal communication with the heater 46 to surround the circumference of the molten salt reservoir in order to thermally insulate the interior of the droplet generator 22 from the ambient environment. In another embodiment the droplet generator 22 is located within an oven where the oven gas temperature is sufficient to maintain the salt in a molten state. In embodiments using induction heaters, the induction heaters are positioned within the interior of the droplet generator, disposed such that the induction heater contacts and approximates the inner diameter of the cylindrical wall 30. An induction heater internally disposed within the droplet generator contacts molten material when the generator is filled, allowing for heating or re-heating of the molten materials up to about 1000° C.

In an embodiment, a nozzle fitting 220 is reversibly fixed to the bottom 26 of the droplet generator 22 such that the nozzle fitting 220 is concentric with the aperture 38 through the bottom of 26 of the droplet generator 22. (Means for reversibly attaching the nozzle to the generator include a male-female threaded configuration, or a band fastener.) The nozzle defines a downwardly extending cylindrically-shaped member 222 terminating in a first surface 222a and a second surface 222b, wherein the second surface is superior to the first surface.

The second surface 222b defines a downwardly extending frustoconical void 224, which serves to funnel any melt substrate stored within the void 16 defined by the droplet generator. The frustoconical void 224, coaxially arranged with the nozzle, extends approximately one third into the interior of the nozzle, where it terminates in a conduit 226 extending through the remainder of the nozzle. The frustoconical void 224 has the same diameter as the aperture 38 through the bottom surface of the droplet generator 22. When the nozzle 220 is fixed to the droplet generator, the frustoconical void 224 faces the aperture 38 through the bottom of the droplet generator.

The nozzle 220 can be made from any material that will not degrade, deform, or melt when subjected to temperatures up to 400-700° C. Suitable materials include sapphire, stainless steel, low carbon steel, glassy carbon, tantalum, niobium, alumina, cubic zirconia, yttria, yttria stabilized zirconia, yttrium aluminum garnet, boron doped diamond, hafnium nitride, hafnium oxide, zirconium oxide, cubic zirconia, and combinations thereof. Suitable materials are those that are not wetted strongly by the liquid being sampled.

Figure 5A:
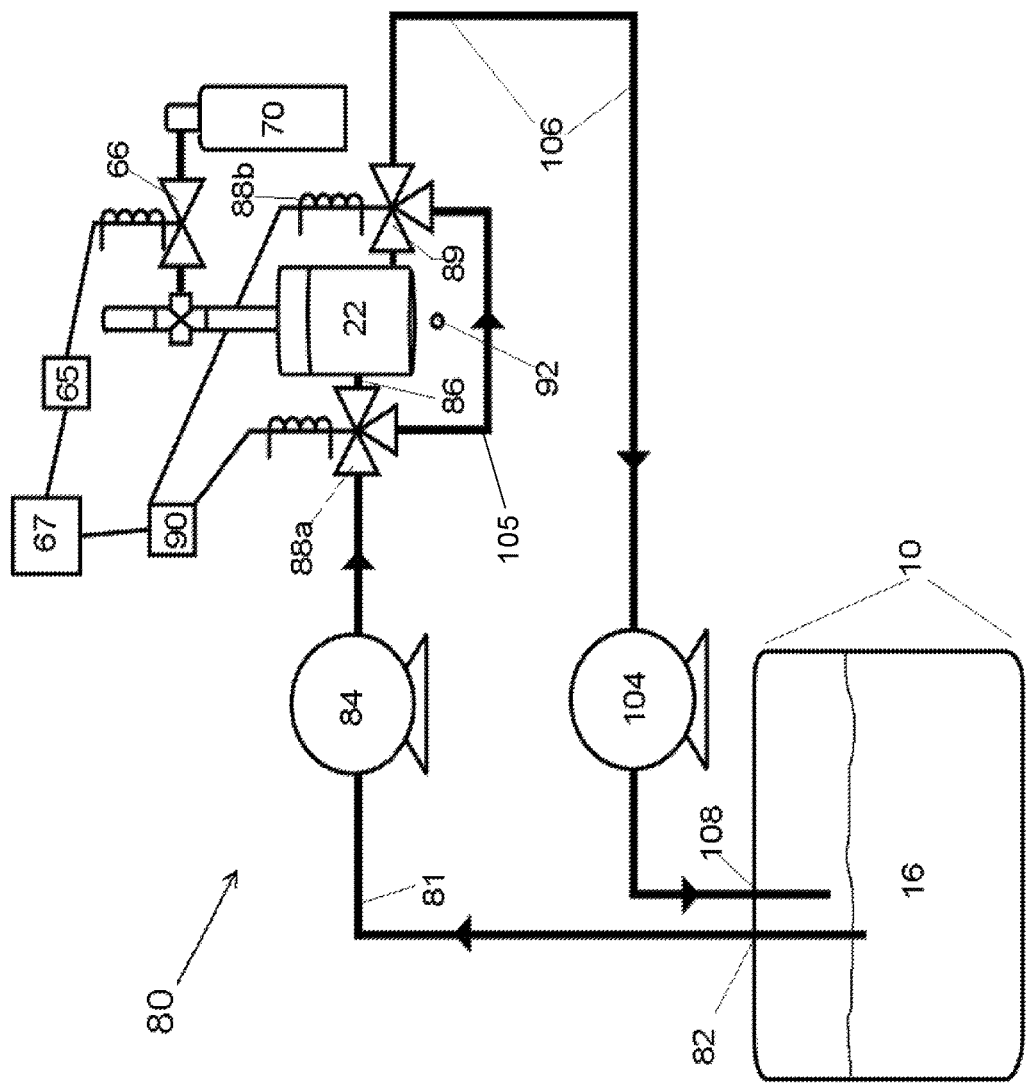
FIG. 5A is a schematic view of an on-line, high-throughput sample generating system for use in monitoring an ongoing electro refining process, in accordance with features of the invention.
Figures 5B, 5C:
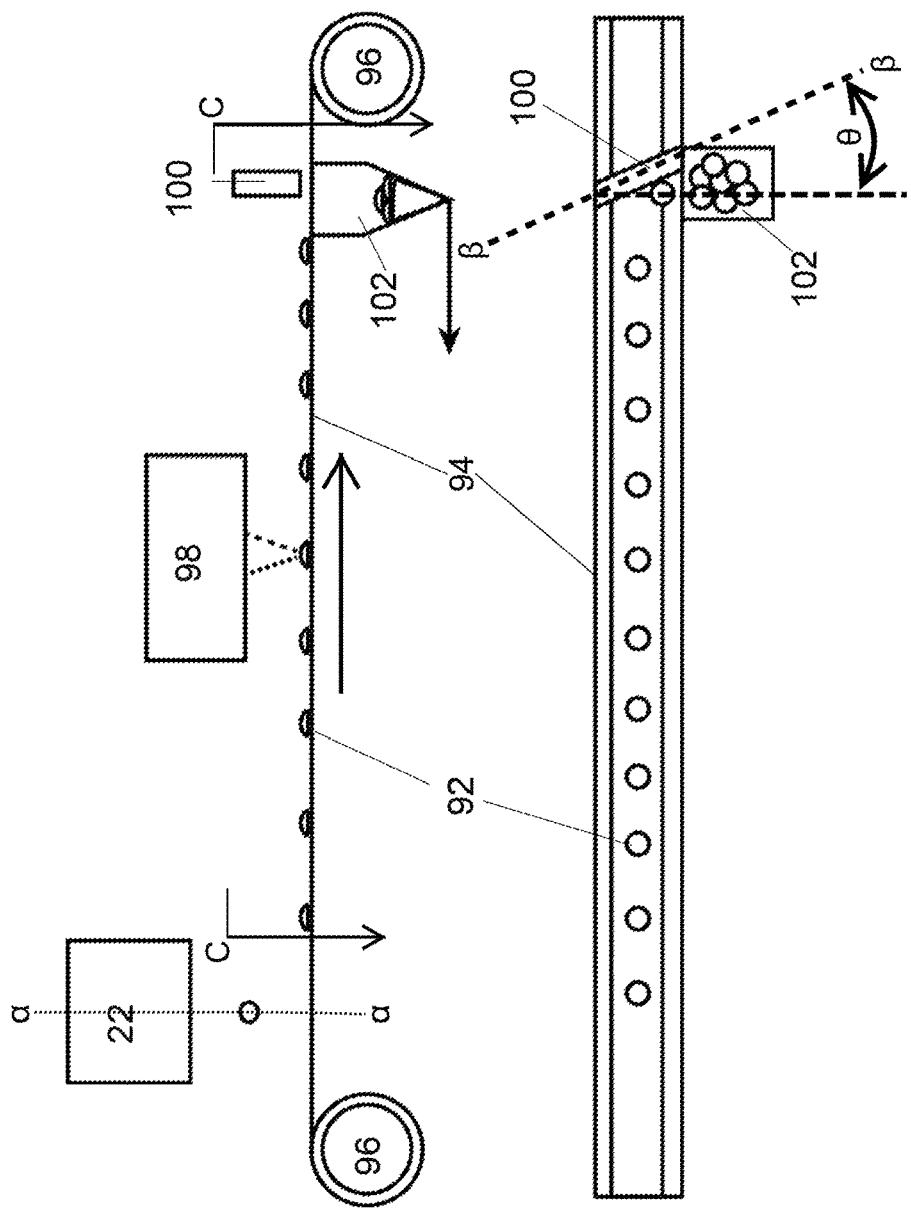
FIG. 5B is a view of a sample transport conveyor system on to which droplets, emanating from the system depicted in FIG. 5A, land in accordance with features of the present invention.
FIG. 5C is a view of FIG. 5B, taken along line C-C, in accordance with features of the invention.
Figure 5D:
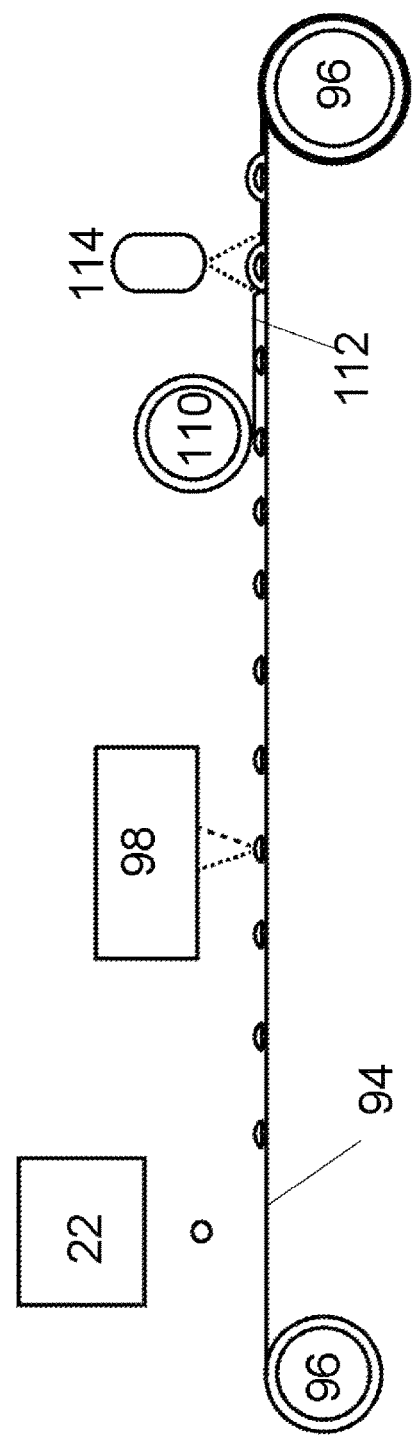
FIG. 5D is an elevational side view of an alternative deposited droplet transport embodiment, in accordance with features of the invention.

The conduit 226 of the nozzle fitting 220 has a diameter which is adapted to receive molten salt to allow formation of a predetermined size drop on the substrate 94 (as depicted in FIGS. 5B-D) beneath it. The conduit 226 diameter is sized so that molten salt electrolyte solution 16 is prevented by surface tension from entering the conduit 226 by gravity only. Rather, an applied pressure, discussed infra, is required so as to provide reproducibly sized droplets. The nozzle 220 is removable and can be interchanged with nozzles having conduits 226 of different diameters to accommodate various melt consistencies and the presence of high solids loads.

Generally, with a molten salt temperature of between about 450° C. and about 700° C., diameters of the conduit 226 between about 0.004 inches and about 0.024 inches are suitable. An experimental apparatus featured a conduit 226 having a diameter of about 0.016 inches. The aperture 42 through the center 44 of the circular lid 34 has a diameter of between about 0.5 inches and about 4 inches. Preferably, the diameter of the aperture is about one inch. As the nozzle member 220 is reversibly fixed to the droplet generator 22, a nozzle member 220 having a conduit 226 with one diameter can be removed and replaced with a nozzle member having a conduit 226 with a different diameter depending on desired droplet size.

The system may comprise a molten salt removal tool to scrape or wipe molten salt residue from the area surrounding the aperture on the exterior surface of the droplet generator. Such a tool comprises a scraper which is actuated by a driver. The driver, when activated, actuates the scraper to remove accumulated materials from the exterior of the droplet ejection aperture and returns the scraper to a resting position out of the pathway of droplet generation when not in use. The scraper is positioned below the downwardly facing surface of the droplet generator aperture at an angle between about 5 and about 90 degrees relative to the longitudinal axis of the droplet generator and comprises a material that will not scratch or otherwise damage the aperture material. The molten salt removal tool allows for facile maintenance of the droplet generator if droplet ejection is not functioning normally (i.e. droplets ejecting at an unintended angle) and is used to prevent or remedy leakage caused by the wetting of the exterior of the droplet ejection aperture with molten materials.

The solenoid valve 66 depicted in FIG. 3A is electrically actuated, transiently pressurizing the droplet generator 22 using an inert gas supplied by a gas source 70. The pressurization of the droplet generator 22 forces out a single droplet of molten salt electrolyte solution 16 from the aperture 38 through the center 40 of the bottom 26 of the droplet generator and through the nozzle member 220. The opening in the valved vent 56 is large enough to allow for venting of excess pressure after a droplet is ejected but small enough to maintain the pressure needed to eject a droplet. Gas remaining in the droplet generator 22 after the ejection of a single droplet of molten salt electrolyte solution 16 exits or otherwise evacuates the droplet generator 22 through the aperture in the center 44 of the circular lid 34 and into the ambient atmosphere through the vent 56. Suitable pressures will be empirically determined based on the constituency (and therefore viscosity and surface tension of the molten salt) and the size of the aperture.

Upon viewing FIG. 3B, in operation, the droplet generator 22 is loaded with molten salt electrolyte solution 16. The conduit 68 intermediate the inert gas source 70 and the normally closed solenoid valve 66 is then pressurized using inert gas from the gas source 70. When sufficient pressure is reached in the conduit 68, the controller 67 signals the power source 65 to send an electrical pulse to the solenoid valve 66. The controller 67 can be programmed to actuate the solenoid valve at preselected time intervals, in response to pressure readings in the conduit 68, or on command from a user. Suitable initial pressures are from about 0.1 psi to about 50 psi, preferably from about 1 psi to 20 psi, and most preferably from about 3 psi to about 15 psi. Desirable initial pressures are empirically determined based on desired droplet size, salt composition, and the diameter of the nozzle conduit 226. Once the solenoid valve 66 is activated and opens, gas flows from the conduit 68 into the droplet generator 22.

The gas pressurizes the droplet generator 22 such that a single droplet of molten salt electrolyte solution is ejected through the aperture 38 through the center 40 of the bottom 26 of the droplet generator 22 and the nozzle member 220. After the droplet is ejected, excess gas leaves the droplet generator 22 through the aperture 42 in the center 44 of the circular lid 34 and into the ambient atmosphere through the vent 56.

A user of the system 20 of FIG. 3A can vary both the initial charge pressure of the conduit 68 and the length of time the solenoid valve 66 remains open, once activated. Both parameters, when varied, cause a change in the volume of the drop ejected from the droplet generator 22, this change determined empirically.

FIGS. 4A-B are graphs showing drop volume as a function of initial pressure in the conduit 68 of FIG. 3A, the time the solenoid valve 66 remains open once activated, and orifice 38 diameter. FIG. 4A is a graph of drop size as a function of time the solenoid valve 66 remains activated (i.e., electrically energized) where the conduit 68 is initially charged to 11 psi. FIG. 4B is a graph of drop size as a function of initial pressure in the conduit 68 where the solenoid valve 64 remains open (e.g., activated) for 4 milliseconds (ms).

Looking to FIG. 4A, where the conduit 68 is initially charged to a pressure of 11 psi, drop volumes range from about 350 nL to about 775 nL where the solenoid 66 of FIG. 4A remains open from about 4 ms to about 9 ms respectively. At a fixed initial pressure in the conduit 68 of FIG. 3A, the volume of the droplet produced from the droplet generator 22 follows an approximately linear relationship where drop volume increases with time the solenoid valve remains activated.

When the normally closed solenoid valve 66 is open for about 4 ms, drop volumes range from about 400 nL to about 700 nL where the conduit 68 is initially charged to about 9 psi to about 18 psi respectively. Where the time the normally closed solenoid valve 66 remains open is fixed at about 4 ms, the volume of the droplet produced from the droplet generator 22 follows an approximately linear relationship where the drop volume increases as initial pressure increases.

While the invented system allows for on-demand generation of droplets of molten salt electrolyte 16 for analysis, additional features enable an on-line, high-throughput system for monitoring an ongoing electrorefining process.

FIGS. 5A-C depict a configuration designated as numeral 80, incorporating the system 20 of FIG. 3, in an on-line, high-throughput system for monitoring an ongoing electro refining process. The system 80 begins by pumping molten salt electrolyte solution (element 16 in FIG. 3) from an electrorefiner 10 of the type shown in FIG. 2 from a sample port 82 in the electrorefiner 10 through a heated conduit 81. Common conduits configurations include ¼" or ½" outer diameter stainless steel tubing. However, conduits of any diameter material capable of carrying molten materials up to about 450° C. to about 700° C. and conducting sufficient heat to keep the materials molten are suitable.

The conduits 81 and 106 are heated using resistive heaters, preferably linear heaters in duplicate (to avoid salt freezing in the lines in case of heater failure). Ceramic or fiberglass heat tape such as XtremeFLEX® BIH and BWH Heavy Insulated Heating Tapes from BriskHeat® (available from BriskHeat Corporation of Columbus, Ohio) are also suitable. Suitable pumping means include metal bellows vacuum pumps, metal diaphragm pumps, and vacuum systems which are thermally tolerant for transporting molten materials within the instant system.

The pump 84 imparts pressure on the still molten electrolyte salt solution 16 so as to cause the fluid to flow to a means of ingress (such as a valved inlet 86) of the droplet generator 22. The ingress valve is actuated via a 3-way solenoid configuration 88a. The 3-way solenoid valve 88a allows for a flow of molten salt electrolyte solution into the droplet generator 22 while in its default (de-energized) configuration. The valve 88a is in electronic communication with a power source 90 that is in electronic communication with the controller 67.

A second pump 104 imparts pressure on the still molten electrolyte solution 16 so as to cause the fluid to flow to a means of egress (such as a valved outlet 89). The valved outlet 89 is modulated via a 3-way solenoid valve 88b. The 3-way solenoid valve 88b allows for a flow of molten salt electrolyte solution out of the droplet generator 22 into the second heated conduit 106 while in its default (de-energized) configuration. The valved outlet 89 is opposite from and below the valved inlet 86. This melt egress means 89 provides an access point of residual melt to be recirculated either to the top of the droplet generator or back to the refiner. In an embodiment, the conduit 81 leading to the means of ingress includes filtering means such as webbing or mesh to prevent passage of solid particles large enough to clog the egress valve 89, aperture at the bottom of the droplet generator, or the nozzle conduit.

The flow-control solenoids 88a, b are de-energized between droplet formations so that molten salt electrolyte flows in and out of the droplet generator 22 through the inlet 86 and outlet 89. The flow rate through the droplet generator 22 between generations of droplets is between about 0.1 and about 1000 m L/min, preferably about 1-about 50 m L/min, and most preferably about 2 to about 10 m L/min. Flow of molten salt electrolyte in and out of the droplet generator 22 allows for sampled droplets to represent the elemental content of molten salt in the electrorefiner over time instead of only representing the content of discrete samples.

During droplet formation, the controller 67 delivers a signal to the instant power source 90 to power the liquid-flow control solenoids 88 a, b, thus switching them to their second configuration so that salt flow to the droplet generator 22 is temporarily rerouted along a by-pass conduit 105. After a set amount of time (between about 0.01 seconds (s) and about 10 s), the power source will send a current pulse to the gas control solenoid valve 66, opening the normally closed solenoid valve 66 to pressurize the droplet generator 22, and causing a droplet 92 to be ejected from the droplet generator 22. A set amount of time after the gas control solenoid valve closes, between about 0.05 sand about 10 s, passes to allow pressure to equalize inside the droplet generator. After pressure equalization, the power to the liquid flow control solenoid valves 88 a, b is stopped, resulting in a switch back to their default configuration and the resuming of flow of molten salt electrolyte solution into and out of the droplet generator 22.

One or both of the 3-way flow-control solenoid valves 88a, b may be configured so that flow into and/or out of the droplet generator 22 occurs in the energized state of the 3-way solenoid valves (and flow into and/or out of the bypass conduit occurs in the de-energized state).

In an embodiment of the invention, the solenoids controlling salt circulation with the electrorefiner are closed for significantly longer than the solenoid controlling the pressure pulse will be open. Optionally, the system may also pause the feed pump 84 and the recirculation pump 104 pump during droplet generation.

A set amount of time after the gas control solenoid valve closes (between about 0.01 s and about 20 s) power is restored to the liquid flow control solenoid valves resuming flow of molten salt electrolyte solution into the droplet generator 22. The chamber/vent acts as a Helmholtz resonator during and after the pressure pulse. It may take a few fractions of a second for the pressure fluctuations to stop after a droplet is generated. Also, the gas line between the line regulator and the chamber may require some time, between about one-tenth of a second and about 10 s to re-pressurize after firing.

Sample Transport and
Analysis Detail

When the droplet generator is activated, a droplet 92 is ejected from the droplet generator 22. The droplet 92 falls to a generally flat, upwardly facing surface of a substrate 94, as depicted in FIGS. 5B-D, and FIGS. 9 and 10. In an embodiment of the invention, the substrate defines a conveyor belt configuration and transports the deposited droplet out from under the generator, so as to make room for another droplet. In other embodiments of the invention, discussed infra, the droplet falls to a non-flat (e.g., concave) region of the substrate.

The substrate extends in a direction that is generally perpendicular to the vertical axis (shown as the dashed line a) of the droplet generator 22. In an embodiment, a droplet 92 falls between about 0.5 cm to about 2 m to the substrate 94, preferably about 0.5 cm to about 15 cm and most preferably about 2 cm to about 8 cm. An embodiment of the invention features a substrate 94 which is a flexible band or belt such that the substrate is in frictional contact with the pair of rollers 96 but not stretched around them. In this embodiment, used substrate 94 is spooled onto the roller 96 down-stream from the droplet generator 22 and collected for decontamination or disposal. Each of the rollers is mounted to allow rotation about their longitudinal axes. One or both of the rollers 96 is motorized to cause movement (shown with a solid arrow) of the substrate 94 in a direction perpendicular to the longitudinal axis of the droplet generator 22. Another embodiment of the invention features a substrate 94 which is a flexible band or belt, such that the substrate 92 is stretched around a pair of rollers 96 so as to be in frictional engagement with the rollers.

Once a droplet 92 falls onto the substrate 94, the substrate 94 moves the droplet 92 through an analysis zone defined by a plurality of detectors 98. Movement of the substrate will pause so that each of the detectors can analyze a droplet 92. The detectors 98 are programmed on a timer or utilize a sensor to begin analysis when a droplet is positioned adjacent to a detector 98. Different types of detectors 98 require different time intervals to perform analysis. Thus, the substrate will cease movement for at least as long as the exposure time required by the detector 98 needing the longest period for analysis. The system 80 is programmed so that droplets 92 are formed as fast as the detectors 98 chosen by a user can analyze a droplet 98 without droplets 92 backing up or landing on top of each other. As the substrate 94 ceases movement for analyzation of a drop 92 when using certain detectors 98, the instant invention analyzes between about 10 and about 5000 drops per hour, depending on the detectors used.

Generally, the droplets 92 on the transporting substrate 94 are in close spatial relationship with the detectors 98 to be scrutinized by the typical detector input means (e.g., optical, thermal, vapor, chemical, physical, etc.). For example, when dealing with optical detection equipment, typically, the input ports of the detectors directly oppose the mass defining each droplet. Line of sight between the detectors may be from above the substrate, from below and through the substrate, from the side of the droplet, or a combination of these.

One or more of the detectors 98 (for example, an X-ray fluorescence detector) are positioned below the substrate 94 such that the longitudinal axis of each of the detectors 98 is parallel to the longitudinal axis of the droplet generator 22 or such that the detectors interrogate the flat surface of the droplet that is in contact with the substrate. Generally, the detectors 98 are adjacent to the substrate 94 such that the longitudinal axis of each of the detectors 98 is perpendicular to the direction of movement of the substrate 94.

The substrate 94 can be made of any material that does not degrade significantly when subjected to elevated temperatures (between 50° C. and 700° C., depending on the time the droplet is allowed to cool while falling). Materials suitable for use as substrate 94 are single- or multiple layers of glass, ceramics, metallic film, or various polymers (polyimide, polypropylene, bi-axially oriented polyethylene, etc.) and combinations thereof. An exemplary substrate is polyimide X-ray fluorescence film. If the droplet landing site of the substrate is non-flat (such that the landing site forms a depression, concave region, or a well), then the droplet generator can be configured such that the droplet emanating therefrom is of a volume and size which allows the molten material to substantially cool to a solid before contacting the substrate. In such instances, a wide range of transport substrate materials can be utilized. Alternatively, the droplet can be configured so as to solidify upon gathering within the well.

The substrate 94 may be cooled by directing an inert fluid such as a gas at a lower temperature than ambient temperature at the substrate 94. Cooling the substrate 94 allows for larger droplets 92 to cool to instrument-friendly temperatures quickly. Alternatively, cooled gas (cooler than ambient temperature) is directed at the flight path of the droplet 92 to the substrate 94 in a direction parallel to the longitudinal axis of the droplet generator 22 as to not disrupt the flight path of the droplet 92.

In other instances, it is desirable to meter out exact quantities of solid spherical samples for off-line analysis. Here, the salt is allowed to fall through a cooling gas until it freezes, which could be up to 2 meters depending on the droplet size and initial temperature. Samples are then collected into a vial or in recessed structures (wells) on a substrate (shown as element 272 in FIG. 10, discussed infra). The small solid spherical particles, once collected, are in a pourable sample form which is more convenient to work with than samples collect by traditional dip tube methods. Alternatively, droplets are quenched and thereby cooled in low surface tension heat transfer fluid (e.g., Duratherm S, available from Duratherm Extended Life Fluids of Lewinston, N.Y.) in order to collect spherical droplets for off-line analysis.

Upon ejection, a droplet 92 begins to cool and continues to do so while moving on the substrate 94 such that the droplet 92 is approximately 30° C. by the time it reaches the first detector 98. Considering the low temperature of the droplets by the time they reach the detectors 98 venue, many room temperature analytical devices can be used as detectors 98. Because each droplet 92 has a volume in the micro- or nanoliter range, the droplets 92 contain only small amounts (between about $2 \times 10^{-7}$ Ci for 10 nL droplets to $2 \times 10^{-3}$ Ci for 1 mL droplets) of radioactivity such that each droplet 92 emanates radiation at levels that will not damage or overwhelm the detectors.

Due to the high temperatures and radiation of the molten salt electrolyte, state of the art in situ monitoring of ongoing electrorefining of used nuclear fuel is limited to methods, such as voltammetry. These methods are still under development and provide only limited composition information. By contrast, the instant invention can utilize any analytical method for analyzing a droplet 92 in order to obtain complete and accurate composition information. Exemplary analytical methods or detectors 98 include alpha particle spectroscopy, beta particle spectroscopy, gamma ray spectroscopy, X-ray fluorescence spectroscopy, laser induced breakdown spectroscopy (LIBS), high resolution X-ray analysis, hybrid K-edge densitometry, neutron spectroscopy, UV-vis spectroscopy, infrared spectroscopy and combinations thereof. The invention can accommodate use of any number of detectors 98 along the substrate 94.

Additionally, two or more droplets may be spotted onto a substrate on top of each other, or in close proximity to each other so that analysis may be performed on multiple droplets at once. This may be desirable for some detector types. For example, several droplets in close proximity may improve the signal for gamma ray spectroscopy, while the thickness of several droplets stacked on top of each other may improve LIBS analysis by preventing laser ablation of the substrate.

Droplets 92 can also be taken for off-line analysis using inductively coupled plasma mass spectrometry, (nano)-liquid chromatography, nuclear magnetic resonance, X-ray diffraction, and X-ray photoelectron spectroscopy.

Droplets will travel between about 0.1 m and about 3 m on the substrate 94 to get to the first detector 98. Detectors 98 may be positioned behind radiation shielding to prevent damage and background interference from radiation emanating from the electrorefiner 10 contents.

The detectors operate at ambient temperature near an electrorefiner for electrorefining used nuclear fuel. Ambient temperature is defined herein to be between about 10° C. to about 150° C., and typically between about 40° C. and about 130° C. Generally, the system 80 is thermally insulated from the active electrorefiner 10 as to avoid damage to the system 80 caused by the heat from the electrorefiner. In an embodiment of the invention, the system 80 is thermally insulated from an active electrorefiner by placing the system a suitable distance from the electro refiner (e.g., about 3 meters) to take advantage of the insulative effects of air. Alternatively, the droplet generator 22 is adjacent to the electrorefiner with the detectors 98 about three meters from the electrorefiner. In this embodiment, the detectors 98 and the electronic components of the system 80 adjacent to the electrorefiner are shielded from radiation emanating from the electrorefiner and thermally insulated using ceramic fiber or other suitable insulating means.

After the droplets 92 are transported by the substrate 94 past the detectors 98, they may be collected via gravity as they fall off the downstream end of the substrate, or they may be scraped or otherwise removed from the substrate by a scraper or diverter 100. The diverter 100 defines a continuous webbing and is positioned above the upwardly facing surface of the deposition substrate at an angle (e.g. about 90 degrees) relative to the longitudinal axis of the deposition substrate 94) so as to facilitate removal of the droplets from the substrate to a proximally located retrieval bin, such as a heated chamber 102. The diverter 100 is positioned over the substrate 94 at a height such that the member 100 does not touch the substrate 94, but still close enough to the substrate such that the droplets 92 cannot pass under the member 100.

The diverting member 100 may be positioned at an angle θ (shown in FIG. 5C) with respect to the direction of movement of the substrate 94 such that droplets 92 are directed off the substrate 94 after making contact with the diverting member 100 and into a collection chamber 102, which may be heated. The chamber 102 heats the droplets 92 until molten where a second pump 104 pumps the re-melted droplets 92 through a second heated conduit 106 and back into the electrorefiner 10 through a return port 108. This feature enables the system to continuously pump salt back into the electrorefiner.

FIG. 5C is a plan view of the substrate 94 and diverting member 100, which is positioned beneath the droplet generator 22. As discussed above, the substrate transports droplets 92 after ejection from the droplet generator 22 (direction of movement shown using a solid arrow) eventually causing the droplets to contact the diverting member 100. The diverting member 100 is positioned at an angle θ with respect to the direction of movement of the substrate 94 such that droplets 92 are forced along the longitudinal axis 13 of the diverting member 100 until the droplets 92 fall off the substrate and into the chamber 102.

Optionally, and as depicted in FIG. 5D, the droplets 92 are sealed after analysis for further off-line analysis, storage, or transport. In this instance, the diverting member 100 of FIG. 5B, C is replaced with a spool 110 wrapped with a retaining substrate 112 such as a polymer film, glass sheet, or metallic foil. The spool 110 is positioned over the center of the substrate 94 downstream from the detectors 98 at a height sufficient for droplets 92 to pass under. The retaining substrate 112 is initially positioned as to contact the surface of the substrate 94 so that the retaining substrate overlays a droplet 92 transported by the substrate 94. Spool 110 may be motorized to cause the substrate to unspool at the same linear rate as the substrate 94 is moving so that the next droplet 92 on the line will contact retaining substrate 112 not already retaining a droplet 92. Alternately, the retaining substrate 112 may be unspooled by the force of the moving substrate after the substrate is sealed to the moving substrate as discussed infra.

Down line from the spool 110 is a means for treating 114 the overlayment 112 material once the material has been dispensed from its spool 110. Suitable treating means include sealing devices that can use either heat (such as that generated by a laser) or pressure to seal the droplets 92 within the retaining substrate 112. Once the droplets 92 are sealed, they can be transported off-line for further analysis or for archiving. In an embodiment of the invention, sealing causes a hermetic seal to form over the droplets so as to substantially eliminate any fluid communication between the droplets and the ambient atmosphere. In an embodiment of the invention the substrate and sealing material are flexible glass, and the sealing method is laser frit sealing.

The spool 110 with the retaining substrate 112 and sealer 114 may be positioned downline from the diverting member 100. As such, the diverting member can be removed or rotated away from the substrate 94 such that the member 100 does not contact the droplets 92, allowing the droplets 92 to pass to the spool 110, retaining substrate 112 and sealer 114.

A detector 98 may be positioned below the droplet generator so that the detector 98 analyzes a droplet 92 immediately upon ejection from the droplet generator 22. FIG. 5E depicts a schematic of a system, designated as numeral 240, which pumps molten salt electrolyte from an electrorefiner 10 using means similar to that in FIG. 5A. In this system 240, a detector 98 is positioned below the droplet generator 22 such that the detector 98 analyzes a droplet 92 immediately after ejection of that droplet. A suitable detector in this scenario is, but is not limited to LIBS, which comprises laser beam optics 242, and plasma emission collection optics 244). The detector 98 is programmed to begin analysis at a predetermined time point after actuation of droplet generation. Alternatively, an IR beam 246 and detector 248 may be used to detect when the falling droplet 92 is in a predetermined position. The detector is triggered at a certain time point after the IR beam 246 is broken by the falling droplet 92. The system 240 shows a droplet 92 falling into a heating chamber 102 for re-melting of the droplet 92 and returning of the salt to the electrorefiner 10. Alternatively, the droplet 92 falls to the conveyor means of FIGS. 5B-5D.

Diaphragm Droplet Generator Detail

Figure 6A:
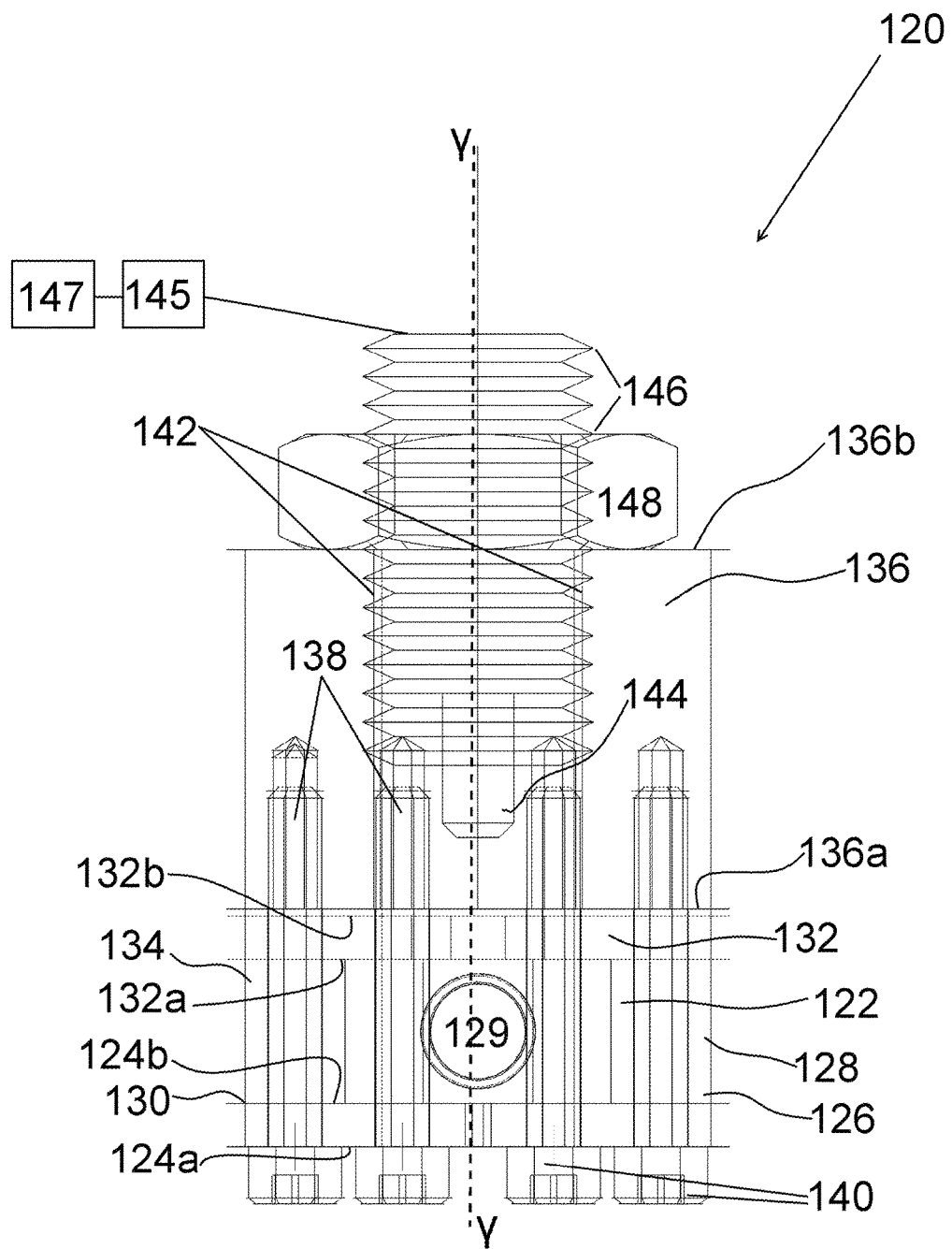
FIG. 6A is a cross-sectional elevation view of an alternative droplet generator, in accordance with features of the invention.

FIG. 6A depicts a sectional view of an alternative embodiment of a droplet generator. This droplet generator includes a molten salt reservoir 122 comprising a cylindrical wall 128 having an interior surface, an exterior surface, a first end 126, and a second end 134.

This diaphragm droplet generator further comprises a medially-facing circular bottom 124 having a first surface and a second surface wherein the second surface of the circular bottom contacts the first end of the cylindrical wall, and wherein the diameter of the circular bottom is at least as wide as the cylindrical wall, wherein the second surface of the circular bottom, interior surface of the cylindrical wall, and first surface of the circular lid define a cylindrical void. The embodiment includes a first aperture through the circular bottom of the molten salt reservoir.

This embodiment of the droplet generator further comprises a circular diaphragm 132 having a first surface 132a and a second surface 132b wherein the first surface of the diaphragm contacts the second end 134 of the cylindrical wall. A cylindrical member 136 having a first surface, a second surface, and a longitudinal extending region disposed between the first and second surfaces is provided wherein the first surface 136a of the cylindrical member is in contact with the second surface 132b of the diaphragm. An aperture is formed through the center of the cylindrical member along the longitudinal axis of said cylindrical member.

A solenoid-actuated pin 144 reversibly inserted into the aperture through the cylindrical member is provided wherein the pin reversibly extends toward, contracts, and causes inward deflection of the diaphragm (along the longitudinal axis γ of the generator) upon actuation of the solenoid.

A flow cell comprising a conduit extending through the thickness of the molten salt flow cell housing of the cylindrical wall's longitudinal axis is provided, wherein the conduit extends in a direction substantially perpendicular to the cylindrical wall's longitudinal axis, and wherein the conduit is in fluid communication with the aperture through the circular bottom of the molten salt flow cell housing. A power source 145 is in electrical contact with the solenoid-actuated pin and a controller 147 is in electrical contact with said power source.

The droplet generator 120 comprises an internally disposed molten salt reservoir 122. As previously discussed, a myriad of reservoir geometries are suitable. For the sake of illustration, a cylindrical configuration is discussed herein. This embodiment features a circular floor or bottom 124 defining a first, downwardly facing surface 124a and second upwardly facing surface 124b. The first end 126 of a cylindrical wall 128 having an interior and exterior surface is integrally molded to the outer edge 130 of the second surface 124 b of the circular bottom 124. Proximal to a lower region of the reservoir, the cylindrical wall 128 defines two apertures 129 through the cylindrical wall 128 wherein the two apertures 129 oppose each other so as to flank the same point of the longitudinal axis of the cylindrical reservoir.

A reversibly deformable circular diaphragm 132 having a diameter equal to or less than the inner diameter of the salt reservoir 122 is positioned superior of the apertures 129 such that the apertures reside between the diaphragm 132 and the floor 124 of the generator. The diaphragm 132 defines a first downwardly facing surface 132a and second upwardly facing surface 132b wherein the first downwardly facing surface 132a contacts the second end 134 of the cylindrical wall 128.

A flow cell 123 (shown in FIG. 7B) comprising a void defined by the first surface of the diaphragm 132a, the second surface of the upwardly facing surface of the circular floor 124b and the interior surface of the cylindrical wall 128 runs between the apertures 129. The flow cell 123 allows flow of molten materials through the droplet generator 120.

Turning back to FIG. 6A, the droplet generator 120 further comprises a cylindrical member 136 having a downwardly facing first surface 136a and an upwardly facing second surface 136b and having the same cross section dimensions (e.g. diameter) as the flow cell housing 122 positioned below it. The cylindrical member 136 is positioned such that the circular diaphragm 132 resides between the circular member 136 and the flow cell housing 122 with all three structures collinear with each other and with the longitudinal axis of the droplet generator 120. The cylindrical member 136 contacts the circular diaphragm 132 wherein the first surface 136a of the cylindrical member 136 contacts the second surface 132b of the circular diaphragm 132. The diaphragm can be made from any material resistant to the corrosion of molten materials, which may be up to about 700° C. Exemplary materials are stainless steel, low carbon steel, tantalum, niobium, and combinations thereof. The first surface of the diaphragm 132 may be coated with materials to prevent corrosion. Suitable coating materials include boron doped diamond, hafnium nitride, hafnium oxide, strontium ruthenate, lithium ruthenate and combinations thereof.

A plurality of threaded apertures 138 extend from the periphery of the first surface 124a of the circular bottom 124, into the cylindrical member 136 and are adapted to receive longitudinally extending fasteners 140 in a male-female configuration so as to removably fasten the cylindrical member 136 to the flow cell housing 122. The fasteners, so deployed, reversibly join the flow cell housing 122, the diaphragm 132, and the cylindrical member 136.

Another threaded aperture 142 extends through the center of the cylindrical member 136 so as to be coaxial with the longitudinal axis of the member (shown as the dashed line γ). A pin 144 having a threaded sheath 146 is fastened into the threaded aperture 142 such that the pin 144 is positioned proximate to and above the diaphragm 132. A nut 148 fastens the threaded sheath 146 to the second surface 136*b* of the cylindrical member 136. The pin 144 is actuated by a linear solenoid actuator which is in electrical communication with a power source 145 operated by a controller 147. In an embodiment of the invention, the nut 148 resides along the longitudinal axis of the generator 120 and on its exterior so as to be adjustable without disassembly of the generator 120. In an embodiment of the invention, the pin 144 is fixed to the second upwardly facing surface of the diaphragm 132*b* wherein the pin 144 is actuated by a piezo linear actuator wherein the pin is thermally insulated from the piezoelectric element. In another embodiment of the invention, the pin 144 is removed and diaphragm deformation is actuated via pressurizing means similar to the pressurizing means depicted in FIG. 3A. In another embodiment of the invention, a diaphragm stop (shown as element 149 in FIG. 6B), comprising a fixed pin or an adjustable screw is used to limit diaphragm deformation. The diaphragm stop is mounted on or through the flow cell and is positioned to contact the first inwardly facing surface of the diaphragm 132 upon diaphragm deformation. The diaphragm will cease to deform inwardly when it reaches the diaphragm stop 149.

In operation, the molten salt will be continuously pumped through the droplet generator flow cell 123 from an operating used nuclear fuel electrorefiner (or other molten salt process vessel) through one of the apertures 129 through the cylindrical wall 128. While the droplet generator 120 is in operation, the volume of the flow cell 123 is filled with molten material such that there is no headspace between the first surface of the diaphragm 132*a* and the molten material. When a sample is desired, the controller 147 transmits an electrical impulse from the power source 145 to the solenoid actuated pin 144. Upon this activation, the solenoid actuated pin 144 extends from the sheath 146 and impacts and temporarily deforms the diaphragm 132. In an embodiment, the sample generation process begins at predetermined, previously empirically determined and then programmed into the system, times. When the solenoid actuated pin 144 makes contact with the diaphragm 132, the diaphragm 132 deforms downwardly into the molten salt flow cell housing 122, reducing the volume of the flow cell 123 (Shown in FIG. 6C).

By reducing the volume of the flow cell 123, pressure increases within the flow cell 123. The pressure generated in the flow cell 123 is sufficient to eject a droplet of molten electrolyte solution from the circular aperture 150 through the center of the circular bottom 124 of the droplet generator 120. A diaphragm 132 having a diameter of 1 inch deforms inwardly between about 10 μm and about 200 μm into the flow cell 123 to generate sufficient pressure to eject a droplet. Suitable pressures to generate a droplet are empirically determined based on melt consistencies and on diaphragm diameter and range from about 0.1 to about 100 psi. Droplets generated using this embodiment of the droplet generator 120 will be similar in volume to the droplet generator of FIG. 3 (between approximately 1 nL and approximately 1 ml).

Figure 6B:
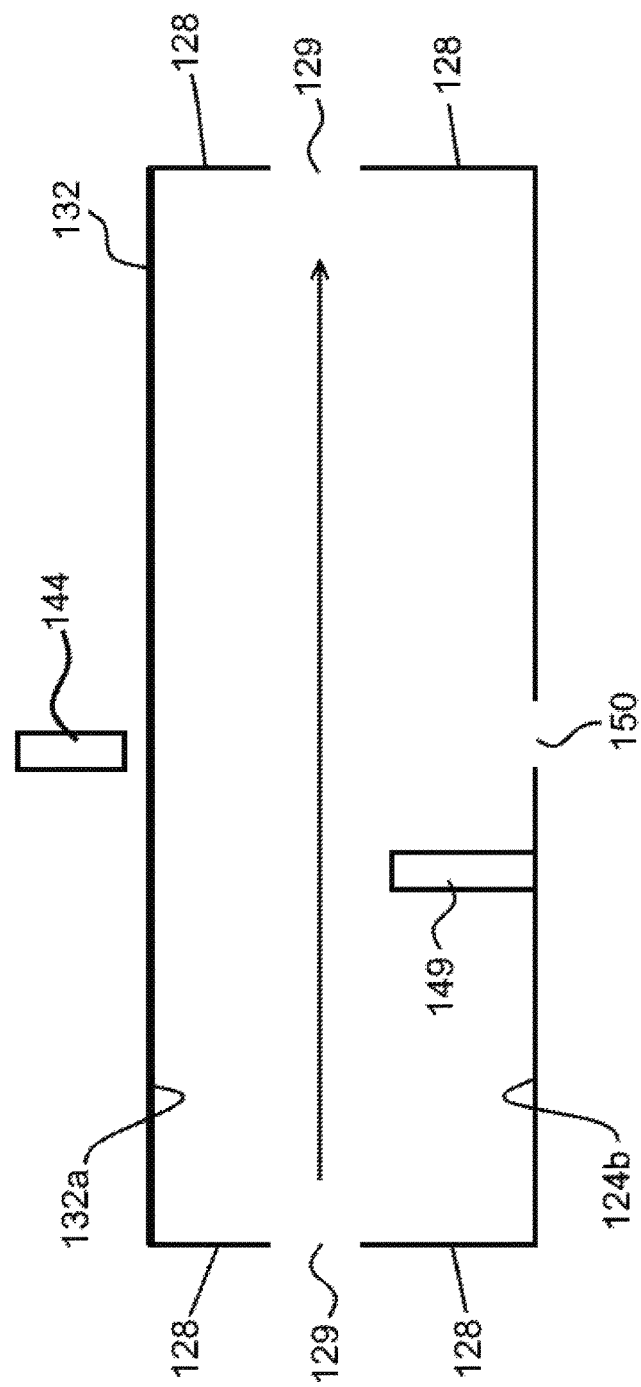
FIG. 6B is a detail view of an alternative embodiment of the flow cell of FIG. 6A, in accordance with features of the invention.

FIG. 6B is a detail of the flow cell FIG. 6A. The cell 123 comprises a void defined by the first surface of the diaphragm 132*a*, the second surface of the upwardly facing surface of the circular floor 124*b* and the interior surface of the cylindrical wall 128 running between the apertures 129 of the droplet generator of FIG. 6A. In operation, molten material continuously flows in and out of the cell (direction of flow indicated with a solid arrow), the molten material filling the volume of the cell such that there is no headspace between the molten material and the first surface of the diaphragm 132*a*.

As discussed above, during droplet generation, the pin 144 is actuated, causing the diaphragm 132 to deform inwardly into the cell 123. Deformation of the diaphragm 132 increases pressure in the cell 123 and causes ejection of a droplet through the aperture 150 through the bottom of the circular floor. A diaphragm stop 149 may be fixed to the cell 123 such that the stop 149 prevents deformation of the diaphragm 132 past the stop 149. The pin 144 and diaphragm 132 are depicted in FIGS. 6A and B as directly opposing the aperture. This configuration is meant to be exemplary and not limiting. The pin 144 and diaphragm 132 may be positioned at any point in the flow cell such that, upon actuation, the diaphragm 132 deformations increase pressure at the aperture sufficiently to generate a droplet.

Figure 7:
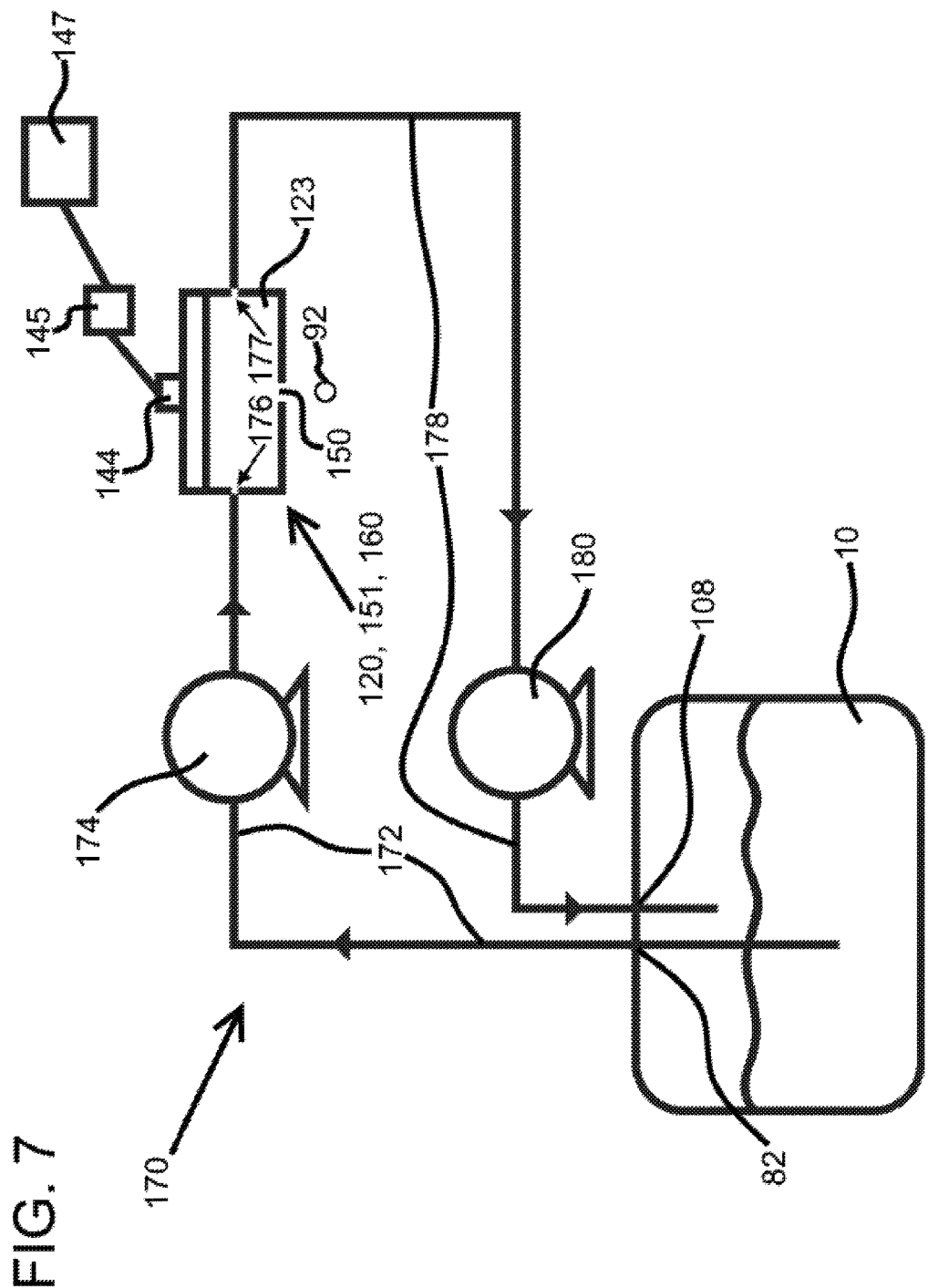
FIG. 7 is a schematic of a system incorporating the droplet generator depicted in FIG. 6, in accordance with features of the invention.

FIG. 6C is a detail view of a preferred geometry of the flow cell 123, so depicted in FIG. 7. The cell 151 is a conduit 152 extending between the apertures 176 and 177 of FIG. 7. In this embodiment, a medial portion of the flow cell conduit 152 is removed such that a portion of the diaphragm's first downwardly facing surface 132*a* is in fluid communication with the interior of the flow cell 151. The conduit may be cylindrical or rectangular in shape. The internal diameter of the flow cell 151 is equal to or less than the internal diameter of the conduit 172 in FIG. 7 that circulates salt to the flow cell. A medial portion 153 of the flow cell conduit 152 defines an aperture such that a portion of the diaphragm's first downwardly facing surface 132*a* is in fluid communication with the interior of the flow cell 151. In an embodiment, the diaphragm 132 is substantially flush with the conduit 152. Alternatively, the diaphragm 132 protrudes partially into the interior of the conduit 152, or is located in a vestibule that extends outwardly beyond the conduit wall. In an embodiment, the flow cell 151 is a cylindrical conduit having an outer diameter of about ⅛ inches to about 1.5 inches.

A region of the flow cell 151 directly opposing the first aperture 153 the flow cell 151 of the droplet generator further defines a circular aperture 150. Alternatively, the apertures 153 and 150 are not directly opposing. In this embodiment, the aperture 153 can be positioned on any point along the length, circumference (in the case of a cylindrical conduit), or perimeter (in the case of a rectangular conduit) of the conduit 152 such that the diaphragm 132 does not restrict ejection of a droplet through the aperture 150 through the bottom of the flow cell 151. Similar to the cell shown in FIG. 6B, a diaphragm stop can be fixed to the conduit 152 to prevent deformation of the diaphragm 132 past a certain point when actuated.

The aperture 150 through the bottom of the cells shown in FIGS. 6B and 6C is adapted to receive melt emanating from the droplet generator. In an embodiment of the invention, the aperture 150 has a diameter of between about 0.004 inches and about 0.04 inches. As in the prior embodiments, pressure and other forces (i.e. capillary forces and surface tension) are balanced to prevent the flow of molten salt electrolyte solution through the aperture 150 without intervention. In an embodiment, the aperture is a cylindrical conduit. In other embodiments, the aperture defines a frustoconical void in fluid communication with a cylindrical conduit as in FIG. 3B.

Optionally, the aperture 150 can be engineered at an angle with respect to the direction of flow of molten salt in the flow cell 160 (shown with solid arrows in FIG. 6D). The angle of the longitudinal axis of the aperture may be chosen such that the ingress end of the aperture 150 points away from the upstream region of the flow cell. The optimum angle to balance fluidic resistances as to prevent leakage will be dependent on the flow rate, temperature and composition of the molten salt, as well as the aperture surface properties and geometry. Generally, the angle is greater than or equal to about 90 degrees and less than about 170 degrees and is most preferably about 130 degrees. This will prevent the melt flow pressure from inducing movement of melt through the aperture 150. An angled aperture 150 prevents stagnant salt accumulation in the aperture and facilitates continual renewal of salt for sampling.

FIG. 6D is a detail view of an alternative embodiment of the flow cell 151 of FIG. 6C. In this embodiment, the flow cell 160 comprises a conduit 161 having a proximal 161a and distal end 161b wherein the diameter of the conduit is substantially the same at the proximal 161a and distal 161 bends. The conduit 161 tapers to a medial portion 162 having a diameter less than that of the proximal 161a and distal ends 161b of the conduit 160. The aperture 150 is formed in the wall of a first region of the medial portion 162 of the flow cell 160.

A second region of the medial portion 162 of the flow cell conduit 161 forms an opening adapted to receive the diaphragm's first downwardly facing surface 132a, such that the surface 132a is in fluid communication with the interior of the flow cell 160. In an embodiment, the downwardly facing surface 132a directly opposes the aperture 150. Alternatively, as with the cell 151 of FIG. 6C, the portion of the membrane 132 exposed to the interior of the cell 160 can be positioned at any point on the conduit 161 such that the diaphragm does not restrict droplet formation from the aperture 150 when actuated. To maintain control of diaphragm deformation, a diaphragm stop can be mounted to the conduit 161 of the cell to prevent deformation of the diaphragm 132 past a predetermined point. The figure shows the second region is positioned superior to the first region of the medial portion. However, this is for illustrative purposes only, inasmuch as the system is not induced by gravity. For example, instead of the horizontal arrangement depicted in FIGS. 6B-D, the configuration may be positioned off horizontal at an angle, or positioned vertically, or "inverted" from that now depicted.

In use, molten salt flows in and out of the flow cell 160 of FIG. 6D through the flow apertures 129. Due to the Venturi effect, the pressure in the proximal 161a and distal ends 161b will be greater than the pressure in narrower medial portion 162 of the flow cell. A pressure drop in the medial portion 162, helps prevent molten salt from leaking through the droplet aperture 150.

Due to the angled aperture and/or flow constriction in FIG. 6D, a slight vacuum is created at aperture 150 under many operating conditions resulting in a low flow of inert gas into the flow cell 160. The inflow of gas facilitates the flushing of the orifice between droplet generation events, so that fresh samples are generated each time.

FIG. 7 depicts a schematic of a system 170 incorporating the droplet generator 120, 151, or 160 of FIGS. 6A-D to create an on-line, high-throughput, continuous system for monitoring an ongoing electro-refining process. The system 170 begins by pumping molten salt electrolyte solution (Element 16 from FIG. 2) from an electrorefiner 10 (or other process vessel or transfer line) of the type shown in FIG. 2 from a sample port 82 in the electrorefiner 10 through a heated conduit 172. A medial portion of the conduit 172 is in fluid communication with a pump 174. Any pump that can handle liquid streams at temperatures near 450° C.-700° C. is suitable for use as a pump within the instant system.

Exemplary pumps include metal diaphragm pumps and centrifugal pumps. The pump 174 propels still molten electrolyte salt solution through the heated conduit 172 into an inlet 176 of the molten salt flow cell 123 representing one of the two apertures 129 of FIGS. 6A-D. The droplet generator 120 also has an outlet 177 representing the other of the two apertures 129 of FIGS. 6A-D. Molten salt electrolyte will flow through the flow cell 123 with a flow rate of about 0.1 mL/min to about 100 L/min, preferably about 5 mL/min to about 10 L/min, and most preferably between about 10 ml/min to about 1 L/min.

While molten salt electrolyte continuously flows into the salt flow cell 123, the controller 147 transmits current from the power source 145 to the solenoid actuated pin 144, which causes the pin to strike the diaphragm 132 and pressurize the salt flow cell 123 as discussed above. With each signal from the controller 147, a droplet 92 is ejected from the droplet generator 120. The controller 147 can be manually operated to activate the solenoid actuated pin 144 and eject a single droplet 92.

Alternatively, the controller 147 is programmed to continuously and at a regular interval send a signal to the power source 145, leading to periodic and continuous ejections of single droplets 92 from the droplet generator 120. Still alternatively, the controller acts in tandem with a call from the detectors when the detectors do not detect a sample for analysis.

Salt that is not ejected through the aperture 150 is returned to the electrorefiner 10 (or other process vessel or transfer line) through a second heated conduit 178 and into the return port 108 of the electrorefiner 10. Optionally, a second pump 180 can be used to increase flow through the flow cell 123. As droplets 92 are ejected from the droplet generator 120, they are collected and analyzed on a conveyor belt system similar to those described above and shown in FIGS. 5B-D or are analyzed immediately following generation as shown in FIG. 5E.

The system 170 of FIG. 7 provides an on-line, high-throughput, continuous system for monitoring an ongoing electro refining process. Advantageously, the droplet generators 120, 151, and 160 of FIGS. 6 and 7 can operate continuously. The only down time for a droplet generator using a solenoid actuated pin and diaphragm to generate pressure is the time it takes for the solenoid actuated pin and diaphragm to reset after firing.

With the continuous nature of the system 170 of FIG. 7, and each droplet having a volume of around 1 µL, the system 120 is high-throughput such that it can generate thousands of droplets per hour (e.g., via a plurality of droplets per second). For example, an embodiment of the invention generates approximately 7200 droplets per hour. Further, the continuous nature of the system 170 returns analyzed droplets 92 back to the electrorefiner 10 without generating waste.

A salient feature of the instant invention is the level of accuracy in monitoring an ongoing used nuclear fuel electrorefining process. As the system 170 is capable of producing thousands of droplets per hour and droplet analysis can be carried out at a rate of up to several droplets per second, depending on the analysis technique, the high-throughput nature of the invention can reduce the effects of random error associated with low throughput or single sample analyses of molten salt. As with the system depicted in FIG. 5A, the system of FIG. 7 can improve the confidence interval of salt composition measurements.

In an embodiment, the droplet generator 120 is positioned at an angle φ from vertical with the molten salt inlet 176 at a position superior to that of the molten salt outlet 177. This embodiment 200 is depicted in FIG. 8. The droplet generator 120, positioned at an angle φ, uses the same general system 120 as depicted in FIG. 6. In this embodiment, however, the first portion of the substrate 202 where a droplet 92 falls from the droplet generator 120 and contacts the substrate 202 is at the same angle φ with respect to vertical as the droplet generator 120. Suitable angles range from between approximately 5 degrees to approximately 85 degrees, preferably between approximately 30 degrees and approximately 60 degrees, and most preferably between approximately 40 degrees and approximately 50 degrees. In an embodiment of the invention, φ is about 45 degrees.

The droplet generator 120 being at an angle with respect to the ground allows a continuous, low-flow through the orifice 150 of FIG. 6A. The salt in this flow does not have sufficient velocity in the direction of the substrate to contact the substrate. Instead it is transported by gravity downward where it is collected and returned to the process. When diaphragm deformation is actuated, a droplet is ejected from the droplet generator onto the substrate. The angled design allows for higher flow rates and pressures, by allowing a slow leak from the orifice. Flow rates are determined empirically with different device angles, and depending on the viscosity of melt and loading of solid fines entrained within same. In the 45 degree embodiment, typical molten material will flow through the droplet generator at a rate of about 0.1 mL/min to about 10 L/min, preferably about 0.1 mL/min to about 10 L/min.

Substrate Detail

In any of the above embodiments, the substrate used to support droplets from a droplet generator can be modified for use with particular melts and analytical methods by modifying the wettability (i.e. the hydrophobicity) of the substrate. Some analytical methods, LIBS, gamma spectroscopy, and neutron spectroscopy, for example, are best suited for analyzing spheroid droplets. Spheroid droplets result from landing on substrates that are not wetted by the molten material.

Conversely, some analytical methods, X-ray fluorescence and alpha spectroscopy, for example, are best suited for analyzing completely flattened droplets, which result from landing on substrates that are wetted by the molten material.

The substrate of the instant invention is customizable to accommodate analysis of droplets using analytical methods best suited for analyzing droplets of a particular shape. FIG. 9 is a side view of a substrate 250 customized for droplet analysis by analysis methods best suited for three different droplet shapes. A first region 252 of the substrate 250 is not wet and a droplet supported by this first region will remain spherical. A second more wet region 254 of the substrate causes a droplet supported thereon to partially deform. A third region 256 of the substrate is the wettest of the three regions, thereby causing a droplet produced using the instant invention to substantially flatten.

In the instant invention, a substrate 250 like that of FIG. 9 can be modified so that subsequent droplets deform to a desired degree for analysis using a predetermined method. For example, provided that the substrate 250 is traveling from left to right (in the direction of the arrow), the first droplet deposited on the third region 256 would be analyzed by a detector best suited for analyzing flat samples 258, the intermediate section 254 facilitating analysis by a method suited to analyzing a spherical droplet 260, and the first region 252 facilitating analysis by a method suiting for analyzing a partially deformed droplet 262. The surface 264 of the substrate 250 can be customized as shown in FIG. 9 or in other configurations so that a substrate is pre-configured so that subsequent droplets are suited for analysis by particular instruments. The configuration of FIG. 9 is exemplary and not meant to be limiting. The surface 264 of the substrate can be pre-configured so that a precise number of subsequently produced drops are suitable for analysis by pre-determined instruments. Surface wettability may be modified by surface treatments, such as silanization, plasma treatment, thin film deposition, and combinations thereof.

FIG. 10 is a side view of a substrate 270 that is molded or etched to create wells 272 wherein the wetness of each of the wells is customized to accommodate analysis of droplets using analytical methods best suited for analyzing droplets of a particular shape. A first well 274 of the substrate 270 is not wet and a droplet disposed in this first well will remain spherical. A second, more wet well 276 of the substrate 270 causes a droplet disposed therein to partially deform. A third well 278 of the substrate 270 is the wettest of the three wells 272, thereby causing a droplet produced using the instant invention to substantially flatten. The surface wetness of the wells 272 can be customized like the surface of the substrate 250 of FIG. 9.

Although many embodiments of the present invention facilitate on-line analysis of molten salt materials, off-line analysis will always be required periodically for performing the most detailed, accurate analyses and for inspection, verification, or calibration purposes. The wells 272 of the substrate 270 of FIG. 10 can receive droplets wherein the wells are subsequently sealed using sealing means as discussed above. After sealing droplet samples into the wells of the substrate, the droplets can be transported to an analytical lab for processing. Many analytical techniques require that the sample be dissolved in an aqueous solution. The well embodiment of FIG. 10 can be used to automate sample dissolution by using a robot programmed to process the sample droplet in each well. Processing is accomplished by piercing the seal on a well with a needle, filling the well with water or other solvent, and then withdrawing the dissolved sample through the needle. This automated sample processing would reduce the radiation incident to workers, and also reduce sampling waste, compared to current sampling techniques, where much larger samples are taken, dissolved and then diluted.

Fluid Pressure Droplet Generator Detail

An alternative embodiment of the invention uses fluid pressure to control droplet ejection from an orifice. In this embodiment, fluid pressure is maintained at or below atmospheric pressure in the orifice region by balancing flow rate, hydraulic head, and cross sectional area. This balance is based on Bernoulli's principle and the Venturi effect, which state that an increase in the speed of a fluid stream results in a decrease in pressure, and that a reduction in fluid pressure occurs as a result of fluid flowing through a constricted section of pipe, respectively.

Figure 11A:
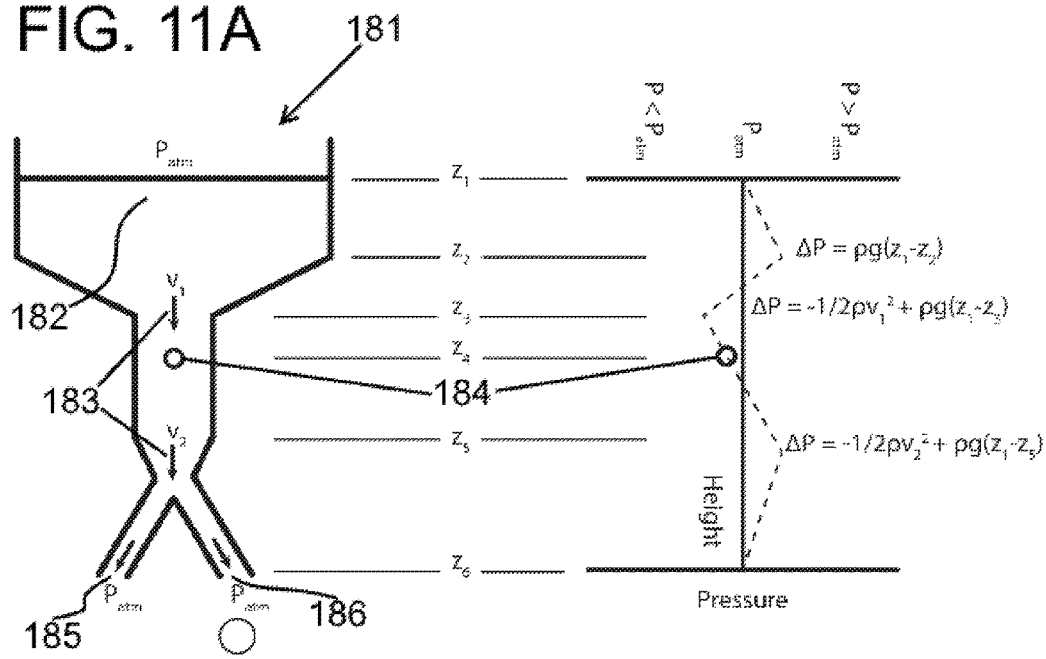
FIGS. 11A-B is a schematic view of the mechanics involved in the operation of the alternative droplet generator depicted in FIG. 12, in accordance with features of the present invention.

In this preferred embodiment of the fluid pressure droplet generator, fluid flow through the droplet generator flow cell is achieved by gravity flow. Gravity flow is preferred because it is reliable and there are no moving pump parts that can fail, making the system robust for remote operation in the harsh environment of a reprocessing facility.

FIG. 11A shows how fluid pressure in a droplet generator gravity flow cell changes with elevation and flow cell cross sectional area and how these two variables are optimized in the invention so that the pressure at the orifice is at or below atmospheric pressure during steady state operation (in-between droplet actuation events). An elevated reservoir 182, a gravity flow cell 183 containing an orifice 184, and two open drains 185, 186 comprise the fluid pressure droplet generator 181. At the surface (height $z_1$) of the molten salt in the elevated reservoir 182, the pressure is atmospheric ($P_{atm}$), because this vessel is open to atmosphere through a vent. The vent contains a vapor trap to prevent salt vapor from exiting the reservoir. The vapor trap consists of a canister containing packing material on which salt vapor will condense, such as stainless steel wool.

Moving lower into the salt in the elevated reservoir, (height $z_2$), the pressure increases due to the hydraulic head of molten salt according to the equation $\Delta P = \rho g(z_1 - z_2)$, where P is the fluid pressure, p is the fluid density, and g is the gravitational constant.

As the fluid flows under the force of gravity down through the flow cell 183 to elevation $z_3$, the cross sectional area of the flow path decreases compared to the cross sectional area in the elevated reservoir 182. This causes the fluid velocity to increase, and the fluid pressure to decrease according to Bernoulli's principle and the Venturi effect. In the flow cell 183 at height $z_3$, the pressure is at a vacuum relative to atmospheric according to the equation $\Delta P = -\frac{1}{2}\rho v_1^2 + \rho g(z_1 - z_3)$, where $v_1$ is the fluid velocity at height $z_3$.

As depicted in FIG. 11, the flow cell upstream of the orifice 184 defines a first cross section or diameter. At or down-stream of the orifice is a region that defines a second cross section or diameter that is less than the first cross section or diameter upstream of the orifice. This flow constriction may comprise a reduced cross sectional area segment located at or downstream of the orifice or at the flow cell outlet 185. Alternately, this flow constriction may consist of a smaller cross sectional area flow cell for the entire length of conduit down-stream of the orifice.

The flow constriction, which may be located anywhere at or between heights $z_4$ and $z_6$, will increase back pressure in the flow cell. The increased back pressure and increasing hydraulic head will result in an increase in fluid pressure to above atmospheric at height $z_5$, according to the equation $\Delta P = -\frac{1}{2}\rho v_2^2 + \rho g(z_1 - z_5)$, where $v_2$ is the fluid velocity at height $z_5$. The fluid pressure will then return to atmospheric pressure at the outlets 185, 186 of the flow cell (height $z_6$), which drains back to the process or to a separate reservoir.

There is a non-fixed position, between height $z_3$ and height $z_5$ in FIG. 11, where the fluid pressure is exactly atmospheric pressure. In the invention, salt cannot leak from the orifice during steady state operation because the orifice 184 is located at height $z_4$ between height $z_3$ and the point of atmospheric fluid pressure. Consequently, the pressure at the orifice is less than or equal to atmospheric pressure and therefor there is no driving force to push salt through the orifice during steady state operation. In the preferred embodiment, the orifice 184 is located closer to the point of atmospheric pressure than the point of minimum pressure (maximum vacuum, height $z_3$), so that droplet generation can be achieved with a small perturbation of the system, such as the actuation methods depicted in FIG. 11 and FIG. 14.

Adjacent or downstream of the orifice 184 is an automated means of briefly reducing the cross sectional area of a region of the flow cell for the purpose of actuating droplet generation. The cross sectional area may be reduced by a variety of means.

Figure 11B:
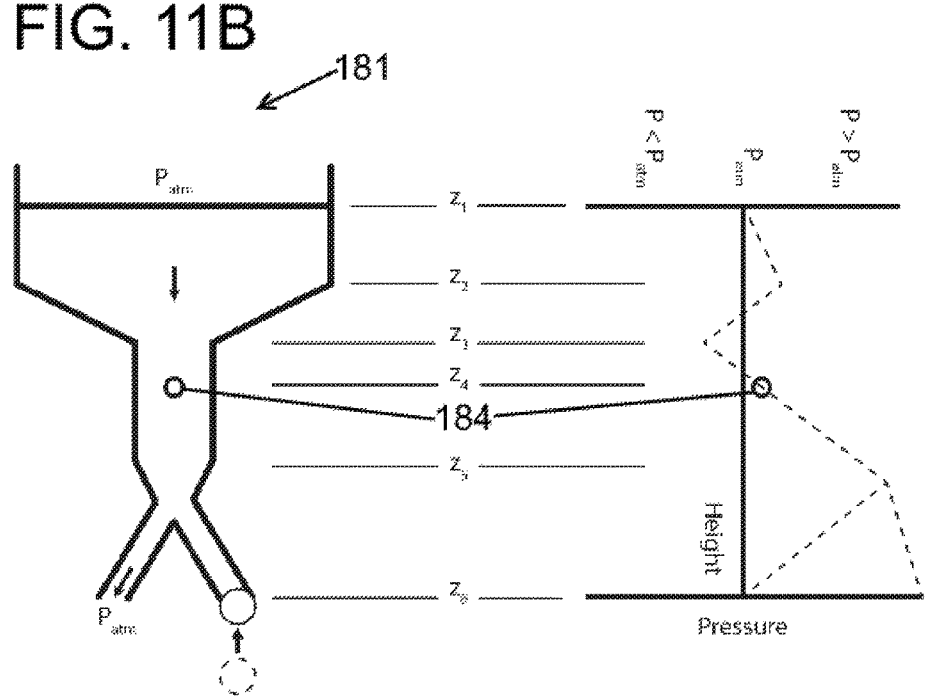

FIGS. 11A and B depict the mechanism of operation for a preferred embodiment of the invention where droplet generation is actuated by decreasing the cross sectional area down-stream of the orifice and increasing back-pressure in the flow cell 183. The cross-sectional area may be decreased by a variety of means. In a preferred embodiment, the flow cell splits into two or more flow paths at some point downstream of the orifice and the cross sectional area is decreased by fully or partially blocking one or more flow paths with an automated valve. A plug valve is preferred for high-temperature applications, and is depicted in FIGS. 11A and B, and FIG. 12 as numeral 188. This causes the point of atmospheric pressure to move from downstream of the orifice (where it is located during steady state operation) to upstream of the orifice, so that the pressure at the orifice 184 rises above atmospheric pressure (FIG. 11B). A pressure above atmospheric pressure at the orifice 184 provides the driving force for the ejection of a droplet.

The flow path downstream of the orifice 184 may be bifurcated. The first leg of the bifurcated region terminates in an aperture for the plug 188, while the depending end of the second leg defines a drain so as to provide a means of egress of molten salt out of the first molten salt line and back into the process vessel 10. During steady state operation (in-between droplet actuation events) the first leg of the bifurcated region provides a means of egress of molten salt out of the first molten salt line and back into the process vessel 10. During actuation of droplet generation the cross sectional area of the flow path is decreased by partially or fully blocking flow in the first leg of the bifurcated region using a second linear operated solenoid operated plug valve 188 (FIG. 11B and FIG. 12).

The actuation event is brief, lasting between 1 and 5,000 milliseconds, and preferably between 10 and 100 milliseconds. At the peak of the actuation event the pressure profile in the droplet generator 151 will be similar to the pressure profile depicted in FIG. 11B and a droplet will be generated. After the actuation event the plug valve will revert to its resting position and the flow will revert to steady state with the pressure profile depicted in FIG. 11A, with no flow through the orifice.

Figure 12:
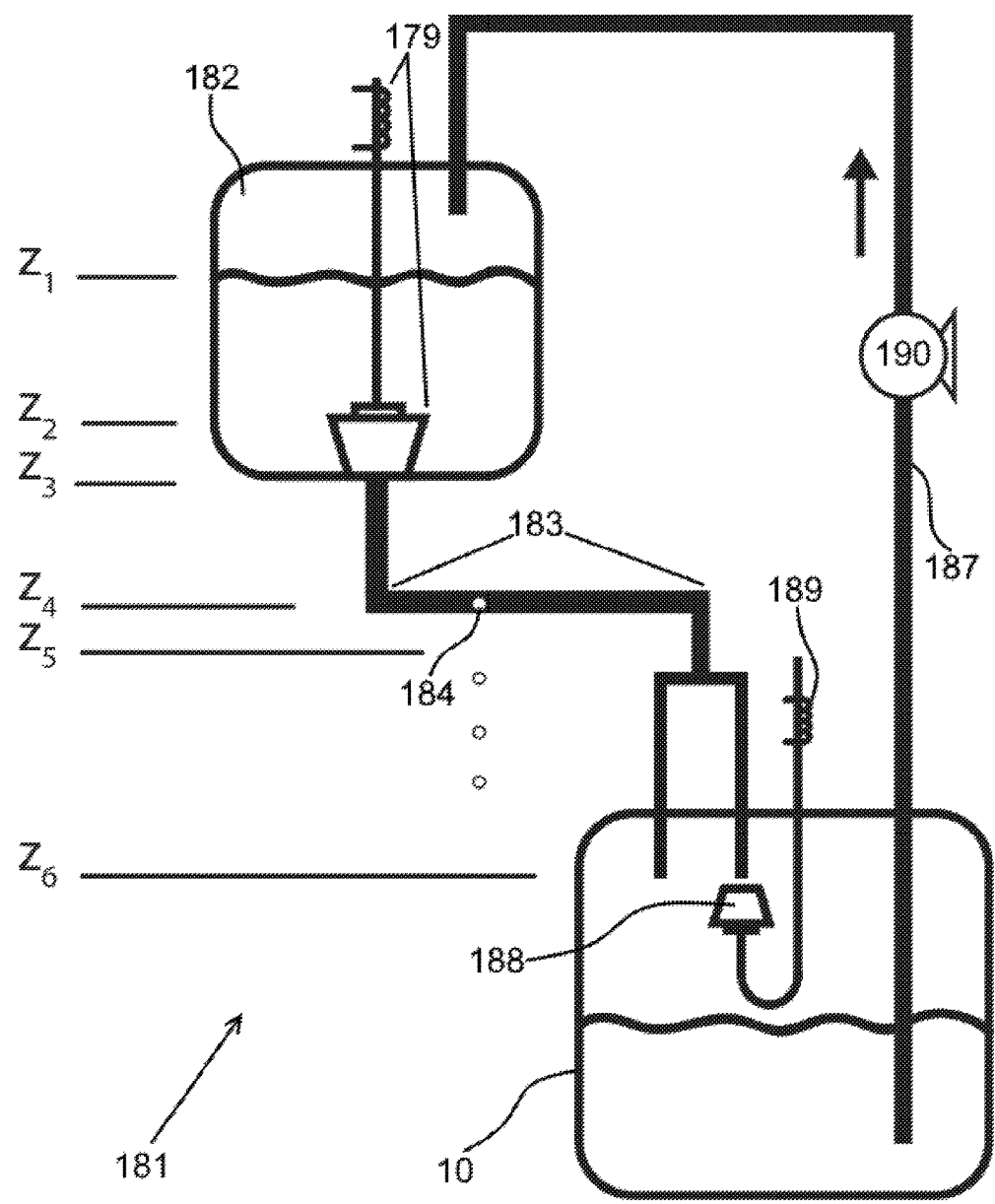
FIG. 12 is a view of an alternative droplet generator, in accordance with features of the present invention.

FIG. 12 depicts the integration of the flow cell in FIG. 11 with a process vessel 10 such as an electrorefiner. The process vessel 10 provides a feedstock for a superiorly positioned upper reservoir 182. Positioned between the upper reservoir 182 and the lower process vessel 10 is a first molten salt line 183 (i.e., the gravity flow cell). Regions of this first molten salt line 183 define an orifice 184 from which salt samples are taken for analysis. A second molten salt line 187 directs molten salt from the process vessel 10 to the upper reservoir 182. This second salt line provides feedstock to the upper reservoir 182 by drawing salt from the lower process vessel 10.

In the preferred embodiment depicted in FIG. 12, an in-line pump 190 in fluid communication with the second molten salt line 187 is positioned between the process vessel 10 and the upper reservoir 182. The pump is operated so as to continuously draw molten salt from the lower process vessel 10 and transport it to the upper reservoir 182 at the same rate as gravity flow is transporting molten salt from the upper reservoir 182 to the process vessel 10. With this continuous flow loop, salt circulates from the process at a rate of approximately 1-100 L/min, while maintaining an approximately constant level of molten salt in the upper reservoir 182. Suitable pumps include but are not limited to centrifugal pumps or metal diaphragm pumps. In one embodiment, a vacuum supply is used to prime the in-line pump 190 with process fluid prior to starting the pump. In the case that a vacuum supply is used to prime the in-line pump, a valve is used on the second molten salt line between the in-line pump 190 and the upper reservoir 182 to seal-off fluid communication with the upper reservoir 182, during the pump priming operation.

Upon fluid pressure droplet generator start-up, the first molten salt line 183 is charged with molten salt upon actuation of a first linear solenoid operated plug valve 179. This first valve is positioned at the bottom of the upper reservoir 182. FIG. 13A is a cross section view of the upper reservoir 182 and the drain means therefore. When the first linear solenoid plug valve 179 is actuated to an open position, salt flows through the first line 183. At the same time as the first solenoid operated plug is actuated (or within a short time frame of each other, about 1-180 seconds), the in-line pump 190 is started so that salt is continuously circulated through the sampling loop and the fluid level in the upper reservoir 182 remains approximately constant. Once salt flow through the gravity flow cell is at steady state (approximately 5 to 60 seconds after starting flow), salt will not flow through the orifice 184 unless droplet generation is actuated.

A plug may be used to prevent salt flows through the orifice during the 5 to 60 seconds of start-up and shut-down of flow through the first molten salt line 183, when the pressure profile differs from the steady state profile depicted in FIG. 11A. The first molten salt line 183 directs molten salt from the upper reservoir 152 back to the process vessel. This first molten salt line is charged with molten salt upon actuation of the first linear, solenoid operated plug valve 179. This first valve is positioned at the bottom of the upper reservoir 182. When the first linear solenoid plug valve is actuated to an open position, a few droplets may emerge from the orifice during the 5-60 seconds before the flow reaches steady state.

The plugs on the linear solenoid operated plug valves in the invention may be either spherical or conical. For the plug valve controlling flow out of the elevated reservoir tank (FIG. 13), the preferred embodiment is a spherical plug with a conical plug housing like the one depicted in FIGS. 13A-C. Flared tubing is the preferred embodiment of a plug housing for the plug valve or valves used to start and stop flow from the lines feeding back into the process vessel 10 from the droplet generator flow cell 183 (i.e. the plug valves at height z6 in FIG. 11 and FIG. 12). The plug used for this plug valve is a conical plug. The plug housings may be fabricated from series 300 stainless steel, while the plugs are fabricated in carbon steel. The plugs or plug housing may be made of steel, stainless steel, tantalum, tungsten or other materials that are compatible with the process fluid. For operation at elevated temperatures the plug and plug housing are made of two different materials to avoid fusing of the two parts.

Figure 14A:
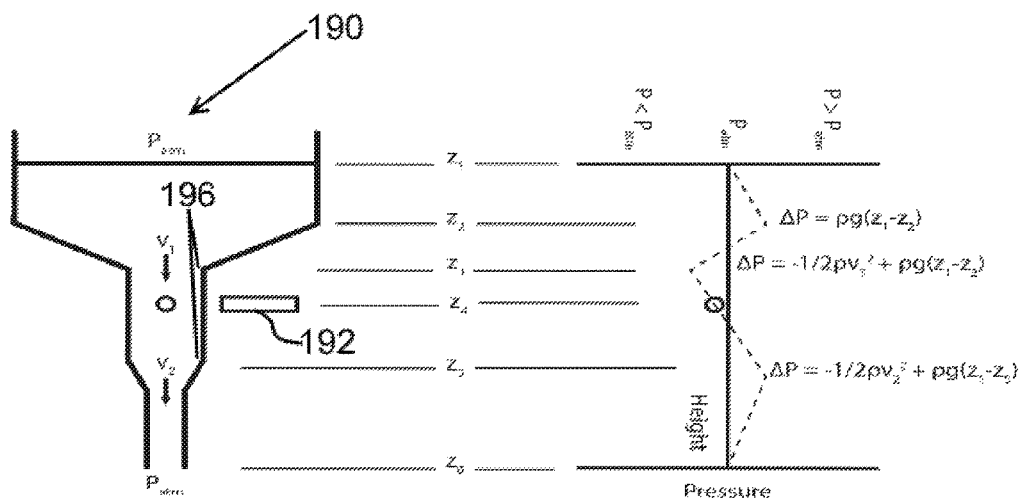
FIGS. 14A-B are schematic depictions for reversibly reducing fluid flow passages, in accordance with features of the present invention.
Figure 14B:
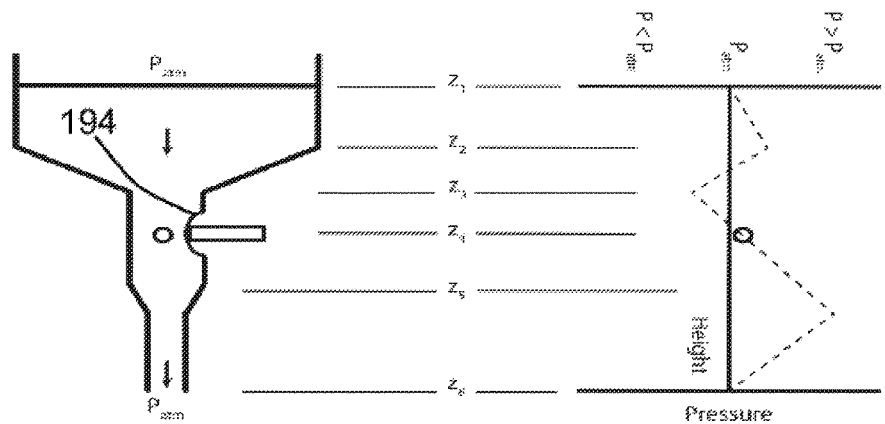

In an alternate embodiment of the fluid pressure droplet generator, the means of reducing the cross sectional area at or downstream of the orifice is a diaphragm as depicted in FIGS. 14A and B. In this diaphragm configuration 190, a plunger 192, actuated by a solenoid, applies a medially directed (relative to the longitudinal axis of the fluid line) force to a membrane 194, the membrane integrally molded with a longitudinally extending region of the fluid line 196. The aforementioned medially directed force urges the membrane into the laminar flow space of the fluid line, so as to protrude within the flow space, so depicted in FIG. 14B. This causes constriction to that flow line. The diaphragm actuated embodiment of the fluid pressure droplet generator may also incorporate any of the diaphragm features described for the diaphragm droplet generators depicted in FIGS. 6B-D.

In embodiments utilizing diaphragms, the invented droplet generator may comprise a molten salt flow cell housing comprising a section of a cylindrical or rectangular conduit. A medial portion of the flow cell conduit contains the membrane and aperture, and has a diameter less than the diameter of the upstream and downstream portions of the conduit. The longitudinal axis of the aperture maybe slanted so that the aperture on the exterior of the conduit is positioned closer to the upstream region of the flow cell than is the aperture on the interior of the conduit. Diaphragm deformation is achieved by piezo-actuation. Wherein a rod (at least partially consisting of a thermally insulating material) is fixed on one end to the diaphragm and at the other to a linear piezoactuator and transmits a linear actuation to deform the diaphragm. Alternatively, diaphragm deformation is achieved by pressurization of a chamber surrounding the exterior surface of the diaphragm. Chamber pressurization is achieved by opening of a normally closed solenoid valve that is in fluid communication with a pressurized gas supply. A pin or screw acting as a diaphragm stop may be present on the interior of the flow cell to limit membrane deformation.

In an alternate embodiment of the fluid pressure droplet generator, flow through the second molten salt line from the process vessel 10 to the upper reservoir is facilitated via vacuum filling (in place of the in-line pump used for continuous transport of molten salt to the upper reservoir in the preferred embodiment). In this case, there is no vent on the upper reservoir and there is a valve on the second molten salt line, which provides a means of sealing off fluid communication between the upper reservoir and the process vessel 10 so that a vacuum can be created in the upper reservoir. For the vacuum filling process, the plug valve 156 at the bottom of the upper reservoir vessel 152 and the valve in the secondary molten salt line 155 are closed, then a vacuum is drawn in the upper reservoir using a vacuum pump that is connected to the upper reservoir through a vacuum supply line. The upper reservoir connection to the vacuum supply line contains a vapor trap, which has the same properties as the vapor trap described for the vent on the in-line pumping embodiment. This vapor trap prevents salt vapors from clogging the vacuum supply line or from entering the vacuum pump. Once sufficient vacuum is reached in the upper reservoir, the valve on the secondary molten salt line is opened and salt is drawn into the upper reservoir.

In an alternate embodiment of the fluid pressure droplet generator, the upper reservoir is not in an elevated position relative to the process vessel being sampled. In this case, the first molten salt line 183 flows into a second reservoir, and a third molten salt line is used to transport salt back to the process vessel 10.

The orifice in the fluid pressure droplet generator may be machined into a stainless steel molten salt line. This section of molten salt line is reversibly sealed with the rest of the salt line for easy removal and replacement, in case of clogging or need to change the orifice size, configuration, or material. An uncoated stainless steel orifice is unlikely to work with the pneumatic molten salt droplet generator because steel is wetted too strongly by molten salt for the surface tension in the salt to hold the salt in the orifice. However, because the fluid pressure droplet generator has a slight vacuum at the orifice during steady state operation (i.e. in-between droplet generation events), surface tension is not required to prevent salt from exiting the orifice and stainless steel orifices work well. Such an orifice is depicted in FIGS. 15A and B. In this embodiment (which is suitable for use with any of the fluid pressure droplet generators described above), a nozzle is created by modifying the flow cell tubing. The nozzle consists of an orifice bored into the tubing with a counter bore 165 around the orifice and a beveled edge 166 on the nozzle tip. This nozzle has a thin periphery, which facilitates good droplet disengagement from the orifice.

A benefit of a stainless steel orifice is that it can be easily re-bored to remove deposits. Another embodiment of the invention includes a drill to re-bore a clogged orifice without removing the orifice containing section of molten salt line from the process.

In another embodiment of the invention, the molten salt line contains multiple orifices grouped together. The secondary orifices can be in operation at the same time as the primary orifice, to generate multiple droplets per actuation event or they can be plugged with a plug made from carbon steel, tantalum or titanium while the primary orifice is in operation. If the primary orifice fails due to clogging or a different orifice is desired, a secondary orifice can be un-plugged and can then be used as the primary orifice. The secondary orifice(s) may be the same diameter, configuration, and material as the primary orifice or may have different diameters, configurations, and/or material compositions to accommodate different sampling needs.

The orifice may also be composed of an orifice piece or nozzle that is fastened over an aperture in the molten salt line. The potential materials for this orifice or nozzle attachment are the same as the potential pneumatic droplet generator orifice materials It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Some electro-refining processes may not produce sufficient change in molten materials for continuous sampling to be necessary. In these processes, the instant invention can be used hourly or more remote intervals to monitor the composition of molten materials in large batches.

While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The present methods can involve any or all of the steps or conditions discussed above in various combinations, as desired. Accordingly, it will be readily apparent to the skilled artisan that in some of the disclosed methods certain steps can be deleted or additional steps performed without affecting the viability of the methods.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A system for analyzing a molten salt electrolyte comprising:
   a) a droplet generator with an aperture surface and a longitudinal axis;
   b) a sample transport mechanism comprising:
      a substrate having a first surface wherein the first surface opposes the aperture surface, a second surface, and a longitudinal axis extending in a direction substantially perpendicular to the longitudinal axis of the droplet generator;
      a plurality of rollers adapted to rotate around their longitudinal axes, wherein the second surface of the substrate is in frictional contact with said rollers, and wherein at least one of said rollers is motorized to cause movement of the substrate in a direction perpendicular to the longitudinal axis of the droplet generator;
   c) at least one detector positioned above first surface of the substrate;
   d) means to remove droplets generated by the droplet generator from the first surface of the substrate;
   e) a heating chamber positioned adjacent to the substrate such that droplets removed from the surface of the substrate are received by said heating chamber; and
   f) a first conduit having a first end and a second end wherein the first end is in fluid communication with the heating chamber and the second end is in fluid communication with a process vessel.

2. The system of claim 1 further comprising:
   a second conduit having a first end and a second end wherein the first end is in fluid communication with an interior surface of the process vessel and the second end is in fluid communication with the droplet generator;

a first pump coupled to the first conduit intermediate the heating chamber and process vessel; and a second pump coupled to the second conduit intermediate the process vessel and droplet generator.

3. The system of claim 2 wherein the first pump continuously supplies molten electrolyte salt from the process vessel to the droplet generator.

4. The system as recited in claim 2 wherein the second conduit comprises
   a) an upstream region, a mid-stream region defining an aperture and a downstream region, wherein the mid-stream region is positioned between the upstream and the downstream region; and
   b) a plurality of fluid passageways defining the downstream region, wherein the passageways have cross section areas that reversibly constrict.

5. The system as recited in claim 4 wherein the upstream region has a cross sectional area that is larger than the cross sectional areas of the passageways combined.

6. The system as recited in claim 4 wherein the constriction of the passageways can be modified in situ.

7. The system of claim 1 wherein the droplet generator generates droplets having a volume between about 1 nL and about 10 mL.

8. The system of claim 1 wherein the at least one detector is a device selected from the group consisting of an alpha particle spectrometer, a beta particle spectrometer, a gamma ray spectrometer, an X-Ray fluorescence analyzer, a laser induced breakdown spectroscopy analyzer and combinations thereof.

9. A system for analyzing a molten salt electrolyte comprising:
   a) a droplet generator with an aperture surface and a longitudinal axis;
   b) a sample transport mechanism comprising:
      a substrate having a first surface wherein the first surface opposes the aperture surface, a second surface, and a longitudinal axis extending in a direction substantially perpendicular to the longitudinal axis of the droplet generator;
      a plurality of rollers adapted to rotate around their longitudinal axes, wherein the second surface of the substrate is in frictional contact with said rollers, and wherein at least one of said rollers is motorized to cause movement of the substrate in a direction perpendicular to the longitudinal axis of the droplet generator; and
   c) at least one detector positioned above first surface of the substrate, wherein the at least one detector is a device selected from the group consisting of an alpha particle spectrometer, a beta particle spectrometer, a gamma ray spectrometer, an X-Ray fluorescence analyzer, a laser induced breakdown spectroscopy analyzer and combinations thereof.

10. The system of claim 9 further comprising:
means to remove droplets generated by the droplet generator from the first surface of the substrate;
   a heating chamber positioned adjacent to the substrate such that droplets removed from the surface of the substrate are received by said heating chamber; and
   a first conduit having a first end and a second end wherein the first end is in fluid communication with the heating chamber and the second end is in fluid communication with a process vessel.

11. The system of claim 10 further comprising:
   a second conduit having a first end and a second end wherein the first end is in fluid communication with an interior surface of the process vessel and the second end is in fluid communication with the droplet generator;
   a first pump coupled to the first conduit intermediate the heating chamber and process vessel; and
   a second pump coupled to the second conduit intermediate the process vessel and droplet generator.

12. The system of claim 11 wherein the first pump continuously supplies molten electrolyte salt from the process vessel to the droplet generator.

13. The system as recited in claim 11 wherein the second conduit comprises
   a) an upstream region, a mid-stream region defining an aperture and a downstream region, wherein the mid-stream region is positioned between the upstream and the downstream region; and
   b) a plurality of fluid passageways defining the downstream region, wherein the passageways have cross section areas that reversibly constrict.

14. The system as recited in claim 13 wherein the upstream region has a cross sectional area that is larger than the cross sectional areas of the passageways combined.

15. The system as recited in claim 13 wherein the constriction of the passageways can be modified in situ.

16. The system of claim 9 wherein the droplet generator generates droplets having a volume between about 1 nL and about 10 mL.

17. A system for analyzing a molten salt electrolyte comprising:
   a) a droplet generator with an aperture surface and a longitudinal axis;
   b) a sample transport mechanism comprising:
      a substrate having a first surface wherein the first surface opposes the aperture surface, a second surface, and a longitudinal axis extending in a direction substantially perpendicular to the longitudinal axis of the droplet generator;
      a plurality of rollers adapted to rotate around their longitudinal axes, wherein the second surface of the substrate is in frictional contact with said rollers, and wherein at least one of said rollers is motorized to cause movement of the substrate in a direction perpendicular to the longitudinal axis of the droplet generator;
   c) at least one detector positioned above first surface of the substrate;
   d) means to remove droplets generated by the droplet generator from the first surface of the substrate;
   e) a heating chamber positioned adjacent to the substrate such that droplets removed from the surface of the substrate are received by said heating chamber;
   f) a first conduit having a first end and a second end wherein the first end is in fluid communication with the heating chamber and the second end is in fluid communication with a process vessel;
   g) a second conduit having a first end and a second end wherein the first end is in fluid communication with an interior surface of the process vessel and the second end is in fluid communication with the droplet generator;
   h) a first pump coupled to the first conduit intermediate the heating chamber and process vessel; and
   i) a second pump coupled to the second conduit intermediate the process vessel and droplet generator.

18. The system as recited in claim 17 wherein the second conduit comprises a) an upstream region, a mid-stream region defining an aperture and a downstream region, wherein the mid-stream region is positioned between the upstream and the downstream region; and
b) a plurality of fluid passageways defining the downstream region, wherein the passageways have cross section areas that reversibly constrict.

19. The system as recited in claim 18 wherein the upstream region has a cross sectional area that is larger than the cross sectional areas of the passageways combined.

20. The system as recited in claim 18 wherein the constriction of the passageways can be modified in situ.

\* \* \* \* \*